(12) United States Patent
Fuhr et al.

(10) Patent No.: US 11,549,851 B2
(45) Date of Patent: Jan. 10, 2023

(54) DEVICE AND METHOD FOR MONITORING THE TEMPERATURE OF A CRYOPRESERVED BIOLOGICAL SAMPLE

(71) Applicant: Fraunhofer-Gesellschaft zur Foerderung der angewandten Forschung e. V., Munich (DE)

(72) Inventors: Guenter R. Fuhr, Berlin (DE); Heiko Zimmermann, Waldbrunn (DE)

(73) Assignee: Fraunhofer-Gesellschaft zur Foerderung der angewandten Forschung e. V., Munich (DE)

( * ) Notice: Subject to any disclaimer, the term of this patent is extended or adjusted under 35 U.S.C. 154(b) by 336 days.

(21) Appl. No.: 16/097,255

(22) PCT Filed: Mar. 31, 2017

(86) PCT No.: PCT/EP2017/000401
§ 371 (c)(1),
(2) Date: Oct. 27, 2018

(87) PCT Pub. No.: WO2017/186328
PCT Pub. Date: Nov. 2, 2017

(65) Prior Publication Data
US 2019/0113396 A1   Apr. 18, 2019

(30) Foreign Application Priority Data

Apr. 27, 2016 (DE) .................... 10 2016 005 070.5

(51) Int. Cl.
*G01K 11/06* (2006.01)
*G01K 13/00* (2021.01)
(Continued)

(52) U.S. Cl.
CPC ......... *G01K 13/006* (2013.01); *A01N 1/0221* (2013.01); *A01N 1/0236* (2013.01);
(Continued)

(58) Field of Classification Search
CPC .. G01K 11/06; G01K 2203/00; G01K 13/006; G01K 17/00; G01K 13/00;
(Continued)

(56) References Cited

U.S. PATENT DOCUMENTS 1,917,048 A   10/1931   Midgley, Jr.
2,955,942 A   10/1960   Fenity et al.
(Continued)

FOREIGN PATENT DOCUMENTS

CA   2748983 A1   3/2012
CN   1419512 A    5/2003
(Continued)

OTHER PUBLICATIONS

English Abstract for CN 103630503 B (2016).
(Continued)

*Primary Examiner* — Gail Kaplan Verbitsky
(74) *Attorney, Agent, or Firm* — Caesar Rivise, PC

(57) ABSTRACT

The invention relates to a method for monitoring the temperature of a cryopreserved biological sample. The invention also relates to a device for monitoring the temperature of a cryopreserved biological sample. The device (10) for monitoring the temperature of a cryopreserved biological sample comprises a sample container (1) having a receiving space (2) for receiving a biological sample (6). The device also comprises at least one chamber (11) having an interior that is not fluidically connected to the receiving space (2) and is only partially filled with an indicator substance (7) with a melting temperature in a region of −20° C. to −140° C. The chamber (11) has a barrier (13) that causes the indicator substance (7) to move into a second sub-region (12b) of the chamber (11) when the indicator substance (7) in a first sub-region (12a) of the chamber is in the fluid aggregate state.

27 Claims, 12 Drawing Sheets

(51) Int. Cl.
  *A01N 1/02* (2006.01)
  *C12M 1/00* (2006.01)
  *C12N 5/0735* (2010.01)
  *G01K 3/04* (2006.01)
  *G01K 11/12* (2021.01)
  *C12M 3/00* (2006.01)

(52) U.S. Cl.
  CPC ............ *A01N 1/0268* (2013.01); *C12M 1/007* (2013.01); *C12M 23/42* (2013.01); *C12N 5/0606* (2013.01); *G01K 3/04* (2013.01); *G01K 11/06* (2013.01); *G01K 11/12* (2013.01); *C12M 23/14* (2013.01); *G01K 2203/00* (2013.01)

(58) Field of Classification Search
  CPC ............ G01K 7/16; G01K 7/20; G01K 7/427; G01K 7/22; G01K 7/24; G01K 17/08; G01K 3/06; G01K 7/25; G01K 11/02; G01K 3/04; G01K 11/12; G01K 1/42; G01K 13/0221; A01N 1/0252; A01N 1/0221; A01N 1/0268; A01N 1/00; A01N 1/0236; B01L 3/50851; G01N 25/18; G01N 33/28; G01N 1/42; B65D 79/02; C12M 23/08; C12M 1/007; C12M 5/0605; C12M 23/42; C12M 23/14
  See application file for complete search history.

(56) References Cited

U.S. PATENT DOCUMENTS

| | | | |
|---|---|---|---|
| RE25,499 E | 12/1963 | Fenity et al. | |
| 3,701,282 A | 10/1972 | Peterson | |
| 3,958,528 A | 5/1976 | Hill | |
| 4,134,359 A | 1/1979 | Redpath | |
| 4,137,049 A | 1/1979 | Couch et al. | |
| 4,163,427 A | 8/1979 | Cooperman et al. | |
| 4,195,056 A | 3/1980 | Patel | |
| 4,280,361 A | 7/1981 | Sala | |
| 4,501,108 A | 2/1985 | Johansson | |
| 4,509,449 A | 4/1985 | Chalmers | |
| 4,664,056 A * | 5/1987 | Jehanno | G01K 11/06 116/217 |
| 4,844,622 A | 7/1989 | Weiss | |
| 5,034,233 A | 7/1991 | McCloy, Jr. | |
| 5,057,434 A | 10/1991 | Prusik et al. | |
| 5,102,233 A * | 4/1992 | Staerk | G01K 11/06 116/217 |
| 5,152,611 A | 10/1992 | Pieper et al. | |
| 5,182,212 A | 1/1993 | Jalinski | |
| 5,282,684 A * | 2/1994 | Holzer | G01K 11/06 116/216 |
| 5,444,989 A | 8/1995 | Gawron et al. | |
| 5,964,181 A | 10/1999 | Pereyra et al. | |
| 6,913,160 B2 | 7/2005 | Bourreau et al. | |
| 7,097,353 B2 | 8/2006 | Wieder | |
| 7,387,438 B2 * | 6/2008 | Parker | G01K 11/06 374/104 |
| 7,415,939 B2 * | 8/2008 | Dip | G01K 11/06 116/216 |
| 8,122,844 B2 | 2/2012 | Smith et al. | |
| 8,168,138 B2 | 5/2012 | Che et al. | |
| 8,173,388 B2 * | 5/2012 | Pasmore | C12Q 1/22 435/31 |
| 9,046,292 B2 | 6/2015 | Burke et al. | |
| 9,097,594 B2 * | 8/2015 | Rastegar | G01K 11/06 |
| 9,222,903 B2 * | 12/2015 | Crevatin | G01N 25/04 |
| 9,279,732 B2 * | 3/2016 | Parker | G01K 11/06 |
| 9,296,500 B2 * | 3/2016 | Childs | B29C 66/81427 |
| 9,464,973 B2 | 10/2016 | Fuhr et al. | |
| 9,618,398 B2 | 4/2017 | Deng et al. | |
| 10,048,138 B2 | 8/2018 | Smith et al. | |
| 10,408,686 B2 * | 9/2019 | Newport | G01K 11/18 |
| 10,917,941 B2 * | 2/2021 | Schryver | G01K 7/22 |
| 2003/0047477 A1 | 3/2003 | Nygardh et al. | |
| 2006/0078036 A1 | 4/2006 | Wieder | |
| 2007/0098039 A1 | 5/2007 | Parker | |
| 2008/0056329 A1 | 3/2008 | Smith et al. | |
| 2009/0129434 A1 | 5/2009 | Creus et al. | |
| 2012/0027045 A1 | 2/2012 | McLellan et al. | |
| 2012/0175412 A1 | 7/2012 | Grabiner et al. | |
| 2013/0068155 A1 | 3/2013 | Patel | |
| 2014/0318437 A1 | 10/2014 | Hong et al. | |
| 2014/0334520 A1 | 11/2014 | Chen et al. | |
| 2019/0075786 A1 * | 3/2019 | Milne | A61M 1/0272 |
| 2019/0113397 A1 | 4/2019 | Fuhr et al. | |
| 2019/0285482 A1 * | 9/2019 | Abdo | G01K 1/02 |
| 2020/0029551 A1 * | 1/2020 | Fuhr | A01N 1/0236 |
| 2020/0362292 A1 | 11/2020 | Hoehse et al. | |
| 2021/0010873 A1 | 1/2021 | Aida et al. | |

FOREIGN PATENT DOCUMENTS

| | | |
|---|---|---|
| CN | 1687757 A | 10/2005 |
| CN | 1809734 A | 7/2006 |
| CN | 101198850 A | 6/2008 |
| CN | 201731955 U | 2/2011 |
| CN | 102369387 A | 3/2012 |
| CN | 102379278 A | 3/2012 |
| CN | 102844649 A | 12/2012 |
| CN | 102853946 A | 1/2013 |
| CN | 104501994 A | 4/2015 |
| CN | 104583741 A | 4/2015 |
| CN | 103630503 B | 4/2016 |
| CN | 205175785 U | 4/2016 |
| CN | 109152354 A | 1/2019 |
| DE | 7461 A1 | 7/1970 |
| DE | 2130926 A | 12/1972 |
| DE | 2504078 A1 | 8/1976 |
| DE | 3435794 U1 | 3/1985 |
| DE | 3712201 A1 | 9/1988 |
| DE | 3716972 A1 | 12/1988 |
| DE | 3731268 A1 | 4/1989 |
| DE | 3838661 A1 | 6/1989 |
| DE | 3940163 A1 | 6/1991 |
| DE | 19960920 A1 | 6/2001 |
| DE | 20301688 U1 | 5/2003 |
| DE | 10203630 A1 | 8/2003 |
| DE | 20301123 U1 | 3/2004 |
| DE | 102005041495 A1 | 3/2007 |
| DE | 102006003995 A1 | 8/2007 |
| DE | 102006003995 B4 | 4/2008 |
| DE | 102006045821 A1 | 4/2008 |
| DE | 102008028334 A1 | 12/2009 |
| DE | 102008031666 A1 | 1/2010 |
| DE | 102008031666 B4 | 5/2010 |
| DE | 102006055331 B4 | 12/2010 |
| DE | 102010052434 A1 | 5/2012 |
| DE | 102011010120 A1 | 8/2012 |
| DE | 102011115467 A1 | 4/2013 |
| DE | 102012202565 A1 | 8/2013 |
| DE | 102013108557 B3 | 11/2014 |
| DE | 102014018308 A1 | 6/2016 |
| EP | 0606033 A1 | 7/1994 |
| EP | 1560009 A1 | 8/2005 |
| EP | 2937850 A1 | 10/2015 |
| EP | 2984928 A1 | 2/2016 |
| FR | 2370269 A2 | 6/1978 |
| FR | 2508164 A1 | 12/1982 |
| FR | 2641611 A1 | 7/1990 |
| FR | 2662798 A1 | 12/1991 |
| FR | 2929705 A1 | 10/2009 |
| FR | 3013836 A1 | 5/2015 |
| GB | 2416842 A | 2/2006 |
| JP | 55-500 A | 1/1980 |
| JP | 56-1322 A | 1/1981 |
| JP | S6055235 A | 3/1985 |
| JP | 60-500460 A | 4/1985 |
| JP | 4-109336 U | 9/1992 |
| JP | H05-99754 A | 4/1993 |
| JP | H07-167716 A | 7/1995 |
| JP | 2002-323386 A | 11/2002 |

(56) References Cited

FOREIGN PATENT DOCUMENTS

| | | | | |
|---|---|---|---|---|
| JP | 2004-77215 A | 3/2004 | | |
| JP | 2006047030 A | 2/2006 | | |
| JP | 2008151716 A | 7/2008 | | |
| JP | 2008542736 A | 11/2008 | | |
| JP | 2009-128137 A | 6/2009 | | |
| JP | 2009-524806 A | 7/2009 | | |
| JP | 4723497 B2 | 7/2011 | | |
| JP | 2012-173282 A | 9/2012 | | |
| JP | 2012219017 A | 11/2012 | | |
| JP | 6893940 B2 * | 6/2021 | ........... | A01N 1/0221 |
| WO | 9802722 A1 | 1/1998 | | |
| WO | 0047964 A1 | 8/2000 | | |
| WO | 2004077001 A1 | 9/2004 | | |
| WO | 2006083892 A2 | 8/2006 | | |
| WO | 2006128899 A1 | 12/2006 | | |
| WO | 2007012132 A1 | 2/2007 | | |
| WO | 2007025589 A1 | 3/2007 | | |
| WO | 2007039094 A1 | 4/2007 | | |
| WO | 2007054160 A2 | 5/2007 | | |
| WO | 2007085385 A1 | 8/2007 | | |
| WO | 2008027814 A2 | 3/2008 | | |
| WO | 2015078767 A1 | 6/2015 | | |
| WO | WO-2018185467 A1 * | 10/2018 | ........... | A01N 1/0257 |

OTHER PUBLICATIONS

English Abstract for CN 205175785 U (2016).
Machine Translation for DD 74651 A1 (1970).
English Abstract for DE 2130926 A (1972).
English Abstract for DE 2504078 A1 (1976).
English Abstract for DE 3712201 A1 (1988).
English Abstract for DE 3716972 A1 (1988).
English Abstract for DE 3731268 A1 (1989).
English Abstract for DE 3838661 A1 (1989).
Machine Translation for DE 8435794 U1 (1985).
English Abstract for DE 10203630 A1 (2003).
English Abstract for DE 19960920 A1 (2001).
English Abstract for DE 20301123 U1 (2004).
English Abstract for DE 20301688 U1 (2003).
English Abstract for DE 102005041495 A1 (2007).
English Abstract for DE 102006045821 A1 (2008).
English Abstract for DE 102008028334 A1 (2009).
English Abstract for DE 102008031666 A1 (2010).
English Abstract for DE 102008031666 B4 (2010).
English Abstract for DE 102010052434 A1 (2012).
English Abstract for DE 102011010120 A1 (2012).
English Abstract for DE 102011115467 A1 (2013).
English Abstract for DE 102012202565 A1 (2013).
English Abstract for DE 102013108557 B3 (2014).
English Abstract for DE 102014018308 A1 (2016).
English Abstract for FR 2370269 A2 (1978).
English Abstract for FR 2508164 A1 (1982).
English Abstract for FR 2641611 A1 (1990).
English Abstract for FR 2662798 A1 (1991).
English Abstract for FR 2929705 A1 (2009).
English Abstract for FR 3013836 A1 (2015).
English Abstract for JP S6055235 A (1985).
Machine Translation for JP 2006047030 A (2006).
Machine Translation for JP 2008151716 A (2008).
3M (2006). 3M Monitor Mark. Time Temperature Indicators. Product Literature, 1-4.
Biocision LLC. (2013). Snap freezing using dry ice or liquid nitrogen. Product Literature, 1-2.
Capture of http://www.cryoguard.com/key-information/ retrieved from internet archive on Jun. 21, 2017.
Durst et al. (2007). Management, interchange and reproducible execution of sample preparation knowledge in collaborative research scenarios. Proceedings of I-Know '07 Graz, Austria. 111-117.
FreezCube (2008). Screenshot from video at 2:23. FreezCube, Invention Géniale? Youtube. Published at https://www.youtube.com/watch?v=ZjPf7YP5r68 on Sep. 22, 2008.
FreezCube (2010). Le gardien de vos surgelees. Product Literature, 1-13.
Germann et al. (2013). Temperature fluctuations during deep temperature cryopreservation reduce PBMC recovery, viability and T-cell function. Cryobiology, 67, 193-200.
Goodell et al. (2016). Ring test evaluation of the detection of influenza A virus in swine oral fluids by real-time reverse-transcription polymerase chain reaction and virus isolation. The Canadian Journal of Veterinary Research, 80, 12-20.
Ihmig et al. (2006). Cryogenic electronic memory infrastructure for physically related "continuity of care records" of frozen cells. Cryogenics, 46, 312-320.
Ihmig et al. (2009). The technology of the global HIV vaccine research cryorepository. Engineering in Life Sciences, 9(5), 376-383.
Ihmig et al. GHRC/CAVD-technology: new identification, storage and distribution technologies for vaccine related reagents and specimens, In AIDS Research and Human Retroviruses (M. Liebert ed. 2010). A68-A69.
Ihmig et al. (2013). Frozen cells and bits: cryoelectronics advances biopreservation. IEEE Pulse, 4(5), 35-43.
Meiser et al. (2009). Entwicklung und evaluierung einer mikrosystem-basierten anlage zur kryokonservierung von multizellulaeren aggregaten. Proceedings of Mirosystemtechnik Kongress, Berlin, Germany, Paper 102.
National Institute of Environmental Health Sciences. (2015). Specimen cold chain SOP—processing, transportation & storage temperatures. Product Literature, 1-6.
Partial Translation for FreezCube (2010). Le gardien de vos surgelees. Product Literature, 1-13.
Partial Translation for Pretschner. (2011). Thermotransportsysteme fuer biomedizische anwendungen. Proceedings of Innovationsforum Bio-Logistik, Leipzig, Germany. Powerpoint Presentation, 75-88.
Pitt et al. (2008). 2008 Best practices for repositories: collection, storage, retrieval and distribution of biological materials for research. Cell Preservation Technology, 6(1), 3-58.
Ren et al. (2009). Evaluation of an outside-the-cold-chain vaccine delivery strategy in remote regions of western china. Public Health Reports, 124, 745-750.
Ruedel et al. (2015). Richtlinie zur probenahme und probenbearbeitung: transport von umweltproben unter cryobedingungen. Umwelt Bundesamt, 1-8.
Shirley et al. (2009). A large-scale cryoelectronic system for biological sample banking. Cryogenics, 49, 638-642.
Simione. (2012). A guide for proper cryogenic preservation. Thermo Fisher Scientific, 1-14.
Thermo Fisher Scientific. (2010). Thermo scientific nunc cryobank vials and bank-it tube system. Product Literature, 1-8.
Thermo Fisher Scientific. (2014). Automated sample storage resource guide. Product Literature, 1-24.
Thermo Fisher Scientific. (2015). Thermo scientific sample storage products. Product Literature, 1-18.
Thermo Fisher Scientific. (2016). The anatomy of the a cryogenic tube. Product Literature, 1-8.
WarmMark. (2014). WarmMark Technical Data Sheet. Product Literature, 1-11.
International Search Report of PCT/EP2017/000401 (dated Jul. 7, 2017).
English Abstract for CN 1687757 A (2005).
English Abstract for CN 201731955 U (2011).
English Abstract for CN 104501994 A (2015).
English Abstract for EP 0606033 A1 (1994).
Machine Translation of Abstract for JP 4-109336 U (1992).
Machine Translation for JP H07-167716 A (1995).
English Abstract for JP 2002-323386 A (2002).
English Abstract for JP 2004-77215 A (2004).
English Abstract for JP 2009-128137 A (2009).
English Abstract for JP 2012-173282 A (2012).
English Abstract for JP 2012219017 A (2012).
Japanese Office Action with Translation dated Nov. 16, 2020.
U.S. Appl. No. 16/095,549, filed Oct. 22, 2018.
U.S. Appl. No. 16/095,591, filed Oct. 22, 2018.
U.S. Appl. No. 16/095,936, filed Oct. 23, 2018.

(56) References Cited

OTHER PUBLICATIONS

U.S. Appl. No. 16/097,111, filed Oct. 26, 2018.
U.S. Appl. No. 16/097,259, filed Oct. 28, 2018.
English Abstract for DE 3940163 A1 (1991).
Chinese Office Action dated Jul. 1, 2021.

* cited by examiner

| | |
|---|---|
| Ammonia | -77.8 |
| Ethyl alcohol | -114.5 |
| Benzol | + 5.5 |
| Bromine | -7.3 |
| Chloroform | -63.5 |
| Diethyl ether | -116.3 |
| Acetic acid | + 16.7 |
| Glycerine | -18.0 |
| Isopentane | -160.0 |
| Methyl alcohol | -97.9 |
| Propyl alcohol | -127.0 |
| Quicksilver | -38.9 |
| Carbon disulphide | -111.6 |
| Carbon tetrachloride | -22.9 |
| Toluol | -94.5 |

FIG. 9

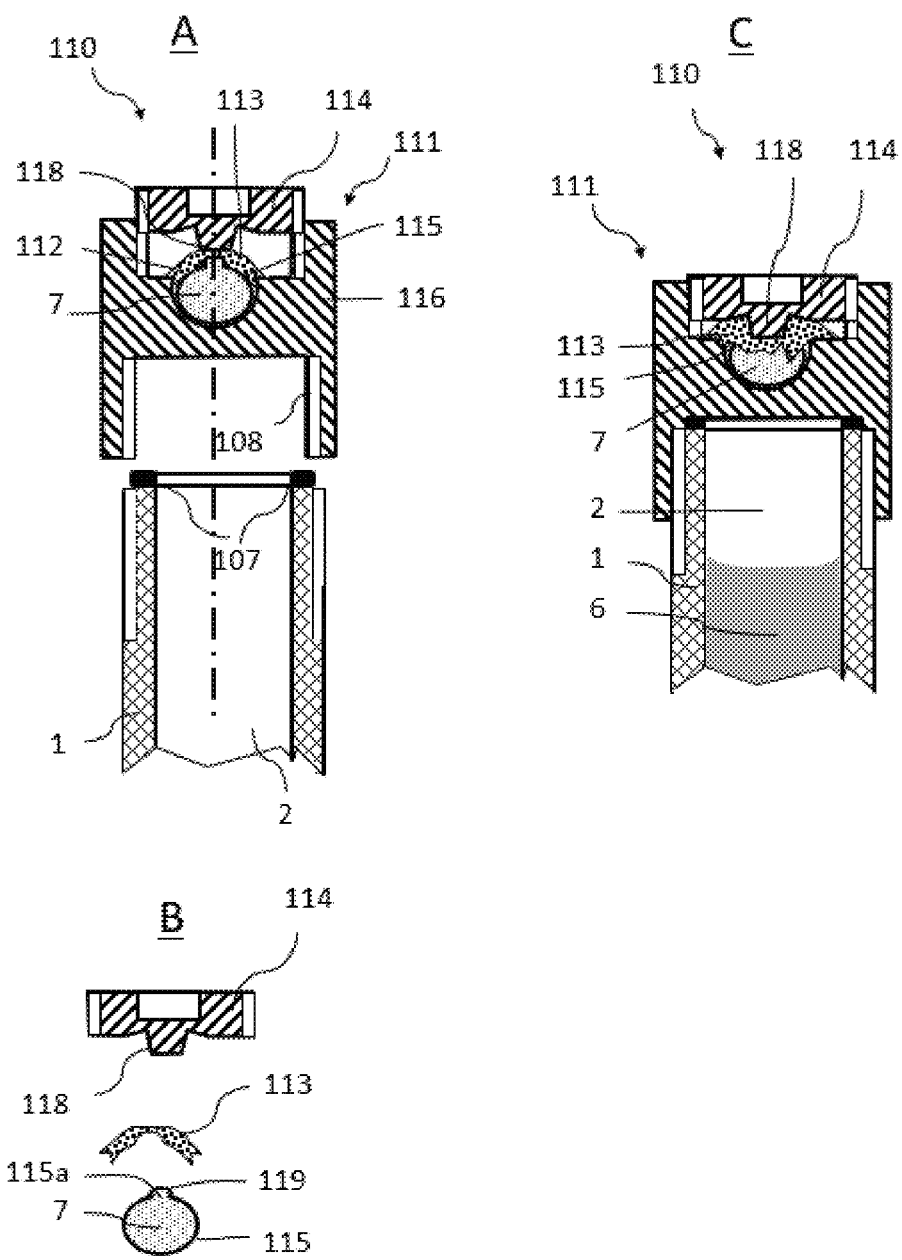

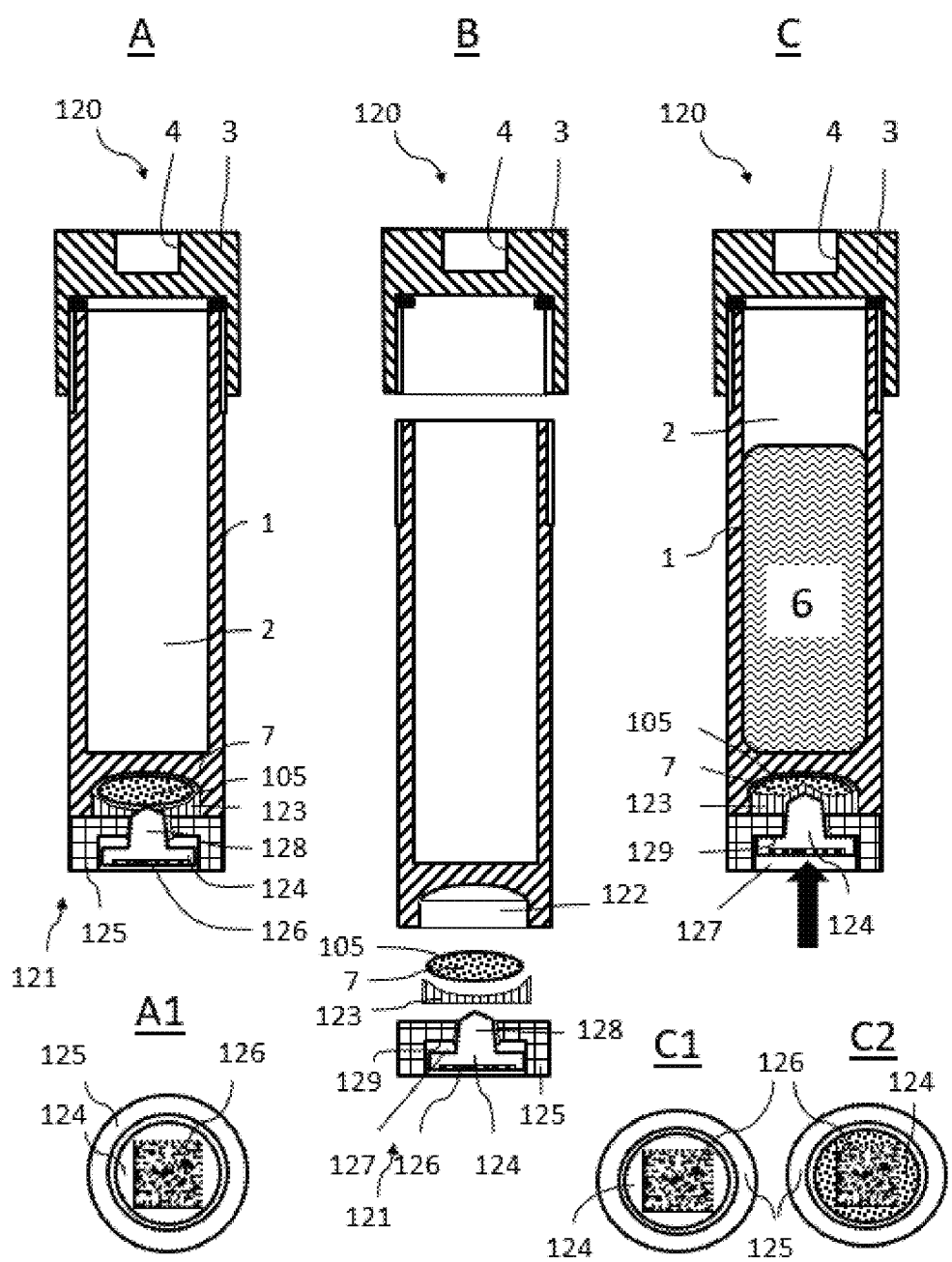

DEVICE AND METHOD FOR MONITORING THE TEMPERATURE OF A CRYOPRESERVED BIOLOGICAL SAMPLE

CROSS-REFERENCE TO RELATED APPLICATIONS

This application is a U.S. National Phase Application of PCT/EP2017/000401, filed Mar. 31, 2017, which claims priority to DE 10 2016 005 070.5, filed Apr. 27, 2016, the contents of which applications are incorporated herein by reference in their entireties for all purposes.

BACKGROUND OF THE INVENTION

The invention relates to a device for temperature monitoring of a cryopreserved biological sample. The invention further relates to a method for temperature monitoring of a cryopreserved biological sample.

The low-temperature preservation (cryopreservation) of cells is hitherto the only possibility of stopping vital processes reversibly (maintaining vitality) at a cellular level such that they can restart after heating to physiological temperatures. Cryopreservation has developed by way of large biobanks in recent decades to become an essential element for clinics, pharmaceutical companies, species survival, environmental protection and health provision. Biological material is stored in low-temperature-compatible sample containers (cryogenic containers), e.g. tubes, straws and bags, of various sizes. In the case of cryopreservation, the stored biomaterial is frozen while maintaining the vitality of the sample material, usually at temperatures below $-80°$ C., for living collections below $-140°$ C. to the temperature of liquid nitrogen. The term "cryogenic sample" is also used below for a cryopreserved sample or a sample intended for cryopreservation.

Numerous techniques have been developed for macroscopic samples, such as e.g. blood or tissue, for sample storage at low temperatures. There is a tendency in modern medicine, genetic engineering and biology to increasingly subject small samples to cryopreservation. For example, small suspension volumes (milliliter or below) with suspended cells or groups of cells are frozen. The cryopreservation of cells from in-vitro cultures is primarily carried out in a suspension. However, the majority of biomedically significant cells require a substrate contact for their propagation and proper development. Samples are therefore frozen in the substrate-bound state possibly after cultivation.

The quality of the samples is of decisive importance since they are used for cell therapies in clinics, the development of pharmaceuticals and biotechnological products, as national resources and many other things. The storage time varies from a few days up to decades, with a tendency towards long-term storage. The samples are stored in cooled containers, are usually located in metal drawers and racks, with which they are subjected to temperature fluctuations in the case of new deposits or removals. In the case of living storage (cells, cell suspensions and pieces of tissue), it is not only the uninterrupted cooling chain which plays a vital role, but also the avoidance of large jumps in temperature in the deep-freezing phase. Since it is not unknown during removal for cryogenic containers to heat up to temperatures of $-80°$ C. to $-20°$ C., despite the fact they are still frozen, reductions in quality unknowingly arise which not only reduce the value of the sample, but can also lead to life-threatening situations when they are used in the clinical sector. Even if samples have only thawed briefly, it is not possible to see in the refrozen state that they no longer match the original condition. However, it is especially important to not only identify a thawing of the biomaterial, but also to document the exceeding of a threshold temperature in the range between $-140°$ C. and $-20°$ C. Temperature control and documentation for each sample is the requirement, one which has hitherto only seldom been satisfied, and if so, with high technical outlay. One must also remember extensive laboratory tests after thawing which also use valuable sample material and generate costs even in the case of cryogenic samples which have become worthless in the interim.

One object of the invention is thus to provide an improved method for temperature monitoring of a cryopreserved biological sample, with which disadvantages of conventional techniques can be avoided and which is characterized by a simplified execution of the method. A further object is to provide a device for temperature monitoring of a cryopreserved biological sample with which disadvantages of conventional techniques can be avoided.

A further object is to provide a possibility in order to be able to identify from as simple as possible a marker whether a cryogenic sample has been heated above a definable threshold temperature, even if only for a short time. It must be possible to fix the threshold temperature in the range between $-20°$ C. and $-140°$ C. prior to freezing. This should be possible quickly and in a readily apparent manner at each individual cryogenic sample and at thus millions of samples, must not change the biomaterials and should already be carried out in the deep-frozen state. If possible it should be possible to detect the condition of the sample even in the storage container since every time the sample is removed from and returned to storage there is the risk of a change in sample of a plurality of samples in the store since entire racks are generally pulled up. The device and the method should be easy to handle, low-temperature-tolerant and adjustable. It must consume no or only a small amount of energy and result in only the smallest of costs since the storage of a biological sample in the cooled state should only cost a few Euros in terms of total outlay. The materials used must also satisfy this requirement. It would furthermore be desirable if not only the exceeding of a threshold temperature to be monitored, but also a measure of the duration of this exceeding could be detected.

These objects are achieved by devices and methods of the invention and are explained in greater detail in the following description with partial reference to the figures.

SUMMARY OF THE INVENTION

According to a first aspect of the invention, the stated objects are achieved by a device for temperature monitoring of a cryopreserved biological sample. The device comprises a sample container with a receiving space (sample reservoir) for receiving a biological sample. The sample container is in particular a cryogenic sample container. The receiving cavity can contain a cryopreserved sample.

The device further comprises at least one chamber, the inner space of which is not fluidically connected to the receiving space and is filled only partially with an indicator substance, the melting temperature of which at normal pressure, i.e. at 1013.25 hPa, lies in a range from $-20°$ C. to $-140°$ C. The melting temperature may preferably also lie in a range from $-20°$ C. to $-100°$ C. In this case, the chamber comprises a barrier which brings about that, if indicator substance is located in a first sub-region of the chamber in the liquid state, this indicator substance reaches a second sub-region of the chamber preferably in a delayed manner, i.e. chronologically retarded. The barrier is not permeable for the indicator substance, if it is frozen. The barrier thus serves as a retardant which is configured to allow a liquid flow in a delayed manned from the first sub-region of the chamber into the second sub-region.

As a result of the chamber of the device according to the invention, an additional compartment is thus provided which may be used as the indicator element or indicator apparatus as a result of the partial filling with the indicator substance in order to display an undesirable exceeding of the threshold temperature. If a threshold temperature to be monitored which corresponds to the melting temperature of the indicator substance or a threshold temperature which lies above the melting temperature and in the case of which a viscosity of the liquefied indicator substance has reduced to a sufficiently great extent is exceeded, the indicator substance becomes liquid and passes from the first sub-region into the second sub-region of the chamber. If at least a part of the indicator substance is thus located in the second sub-region at a later check time, it may be concluded that the threshold temperature was exceeded in the interim, at least briefly.

One particular advantage of the device according to the invention is furthermore that, as a result of the barrier, the indicator substance, upon liquefying, does not immediately fully pass into the second sub-region of the chamber, rather this occurs in a delayed manner and thus requires a predetermined time for this. A measure for the duration of a past exceeding of the melting temperature may therefore be derived from the quantity of indicator substance which is located in the second sub-region at a specific point in time. In this case, the relationship between quantity of indicator substance and duration of the exceeding of the melting temperature may be determined, for example, in advance empirically by tests and provided, for example, in the form of a scale on the chamber wall. The scale may display the corresponding duration of the exceeding of the melting temperature, e.g. as a function of a fill level of the indicator substance in one of the sub-regions or as a function of the length of the diffusion section in the second sub-region.

According to one preferred embodiment, a wall of the second sub-region of the chamber and/or a wall of the first sub-region of the chamber may thus have a scale to display a duration of the exceeding of the melting temperature.

According to a further aspect, a wall of the second sub-region of the chamber and/or a wall of the first sub-region of the chamber may be transparent or semi-transparent at at least one point. As a result, it may be more easily determined whether indicator substance is located in the second sub-region and/or the fill level in at least one of the two sub-regions may be more easily determined. Moreover, the entire chamber may also be manufactured from a transparent or semi-transparent material, i.e. the chamber can be seen from the outside.

For the purpose of improved detectability of changes in configuration, the indicator substance may contain an indicator additive which improves detectability of a physical property of the indicator substance. The indicator additive may be, for example, a dye so that the indicator substance is colored or dyed, i.e. not transparent and thus its presence in the second sub-region can be visually better recognized.

In principle, any dye which satisfies at least the following conditions is possible as a dye:
  intensive dyeing capacity even in small quantities and concentrations (e.g. starting from a saturated dye solution addition in the range <1% by volume, generally in the parts-per thousand or sub-parts-per-thousand range).
  frost-tolerant
  lightfast at the dispatch temperatures and also the relevant low temperatures
  soluble in all components of the indicator substance
  no separation during freezing
  no reaction with plastic materials which come into contact with the indicator substance.

The dye is preferably selected from the group which comprises triphenylmethane dyes, rhodamine dyes, in particular xanthene, azo dyes as well as phenazine and phenothiazine dyes.

In more specific embodiments, the dye is selected from the group which comprises oil red, methyl red, brilliant green, rhodamine B, neutral red, methylene blue or other dyes which are used to dye cells in cytology.

The indicator additive may be particles, in particular nanoparticles which increase a scattering action and/or polarization action of the indicator substance for electromagnetic radiation striking the indicator substance. As a result, e.g. a fill level of the indicator substance in the second sub-region may be detected more reliably by means of optical transmission measurement, scattering measurement and/or polarization measurement. The indicator additive may be conductive particles. The conductivity or impedance of the indicator substance may be influenced by adding conductive particles. In this manner, the presence of the indicator substance may be detected by means of a conductivity measurement or impedance measurement. As a result of the added indicator additive, the corresponding property of the indicator substance may be detected with a correspondingly, expediently configured measuring apparatus in order to be able to more reliably determine the presence and/or a fill level of the indicator substance in the first and/or second sub-region.

The sample container is a container which is suitable for cryopreservation, for example, a tube, a straw (also referred to as a seed tube), a bag for blood or stem cell storage, a box or another container which is suitable for cryopreservation. Such containers are correspondingly also referred to as cryogenic tubes, cryogenic straws, cryogenic bags, cryogenic boxes or generally as cryogenic containers.

Cryogenic tubes are also referred to as biobank or cryobank tubes. Cryogenic tubes have a receiving space which forms an inner cavity for receiving a biological sample. The cryogenic tube furthermore normally comprises a cover for closing off the receiving space. The cover may have an engagement via which the cover can be rotated with a tool. The cryogenic tube may also have a base element which has a marking, e.g. in the form of machine-readable code.

A substance, the melting temperature of which corresponds to a predetermined threshold temperature, the exceeding of which should be monitored, may be selected as the indicator substance. The indicator substance is a liquid or a mixture of different liquids, the melting point of which corresponds to the desired threshold temperature. Merely by way of example, a mixture of water ($H_2O$) and ethanol ($C_2H_6O$), a mixture of water ($H_2O$) and potassium hydroxide (KOH) or a mixture of water and an antifreeze may be selected as the indicator substance. The mixture ratio is adjusted according to the respective melting diagram which indicates the profile of the melting point as a function of the mixture ratio so that the melting point of the liquid mixture has the desired value, namely the threshold temperature to be monitored.

According to one preferred embodiment, the indicator substance comprises at least one alcohol which is selected from the group which comprises octan-1-ol, nonan-1-ol, propane-1,2-diol, propane-1,3-diol, butane-1,2-diol, butane-1,3-diol, butan-2-ol, pentane-1,5-diol, pentan-1-ol, cyclopentanol, benzyl alcohol. The at least one alcohol is particularly preferably selected from propane-1,3-diol, propane-1,2-diol and butan-2-ol.

According to another preferred embodiment, the indicator substance comprises at least two different alcohol components:
a) an alcohol selected from the group which comprises octan-1-ol, nonan-1-ol, propane-1,2-diol, propane-1,3-di ol, butane-1,2-diol, butane-1,3-di ol, butan-2-ol, pentane-1,5-diol, pentan-1-ol, cyclopentanol, benzyl alcohol;
b) an alcohol selected from the group which comprises octan-1-ol, nonan-1-ol, propane-1,2-diol, propane-1,3-diol, butane-1,2-diol, butane-1,3-diol, butan-2-ol, pentane-1,5-diol, pentan-1-ol, cyclopentanol, benzyl alcohol with a lower melting point than the alcohol of component a);
wherein the mixture ratio of components a) and b) is adjusted so that the melting temperature of the mixture lies within a temperature range from −20° C. to −160° C., in particular from −25° C. to −160° C. or −50° C. to −150° C.

More specific embodiments are characterized in that the indicator substance comprises one of the following combinations of components a) and b):
  octan-1-ol and butan-2-ol in a mixture ratio of 5% to 95% by volume;
  octan-1-ol and pentan-1-ol in a mixture ratio of 5% to 95% by volume;
  octan-1-ol and propane-1,2-diol in a mixture ratio of 5% to 95% by volume;
  nonan-1-ol and butan-2-ol in a mixture ratio of 5% to 95% by volume;
  nonan-1-ol and propane-1,2-diol in a mixture ratio of 5% to 95% by volume;
  nonan-1-ol and pentan-1-ol in a mixture ratio of 5% to 95% by volume;
  propane-1,2-diol and butan-2-ol in a mixture ratio of 5% to 95% by volume;
  propane-1,2-diol and propane-1,3-diol in a mixture ratio of 5% to 95% by volume;
  propane-1,2-diol and butane-1,2-diol in a mixture ratio of 5% to 95% by volume;
  propane-1,3-diol and butan-2-ol in a mixture ratio of 5% to 95% by volume;
  propane-1,3-diol and butane-1,2-diol in a mixture ratio of 5% to 95% by volume;
  pentane-1,5-diol and butan-2-ol in a mixture ratio of 5% to 95% by volume;
  benzyl alcohol and butan-2-ol in a mixture ratio of 5% to 95% by volume;
  pentan-1-ol and butan-2-ol in a mixture ratio of 5% to 95% by volume;
  pentan-1-ol and methanol in a mixture ratio of 5% to 95% by volume;
  cyclopentanol and butan-2-ol in a mixture ratio of 5% to 95% by volume;
  cyclopentanol and propane-1,2-diol in a mixture ratio of 5% to 95% by volume;
  cyclopentanol and pentan-1-ol in a mixture ratio of 5% to 95% by volume;
  cyclopentanol and butane-1,2-diol in a mixture ratio of 5% to 95% by volume;
wherein the indicated value of the mixture ratio relates in each case to the ratio of the former component in the mixture of both components.

According to particularly preferred embodiments, this indicator mixture comprises, for example, propane-1,2-diol and butan-2-ol in a mixture ratio of 40% to 60% by volume (produces a melting temperature of approx. −90° C.), propane-1,2-diol and propane-1,3-diol in a mixture ratio of 30% to 70% by volume, or propane-1,3-diol and butan-2-ol in a mixture ratio of 30% to 70% by volume.

The indicator substance preferably also comprises, in addition to the at least one alcohol, at least one dye as described above. This dye is particularly preferably selected from the group which comprises oil red, methyl red, brilliant green and rhodamine B.

An even more specific embodiment is characterized in that the indicator substance comprises at least two alcohols a) and b), which are selected from propane-1,3-diol, propane-1,2-diol and butan-2-ol, preferably in a mixture ratio as indicated above, as well as a dye which is selected from the group which consists of oil red, methyl red, brilliant green and rhodamine B.

The concentration of the dye in the alcohol component can vary greatly depending on the dye and alcohol.

In the case of intensive coloring, the concentration should generally be kept as low as possible so that the dye molecules do not change the freezing and melting properties of the alcohols in which they are dissolved or increase their viscosity. The dye concentration typically lies in a range of <10% by volume, in particular <1% or <0.1%, i.e. in the percent or parts per thousand or sub-parts per thousand range.

In one variant of the present invention, the threshold temperature to be monitored does not correspond directly to the melting temperature of the indicator substance, but rather that temperature above the melting temperature at which the viscosity of the melted substance has reduced to such an extent that the required liquid transport can take place.

This temperature is also referred to here as the threshold temperature and typically lies in a temperature range of 3-30° C. or 5-30° C., for example, 3-10° C., 3-20° C., 5-10° C. or 5-20° C., above the nominal melting temperature.

In one advantageous embodiment, the indicator substance is therefore characterized in that the liquid mixture in a temperature range of 3-30° C. or 5-30° C. above the melting temperature has a viscosity in a range from 10 to $10^6$ mPa*s, preferably 10 to $10^4$ mPa*s.

According to one preferred embodiment of the invention, the barrier may be a material, which is arranged in the second sub-region and adjoins the first sub-region, with a liquid-absorbing structure. The material may be a porous material or medium. The material, e.g. an absorbent mass, may be, for example, filter paper, e.g. such as that of a conventional kitchen roll or a cigarette filter paper, a compact, cellulose discs, e.g. tissue cellulose discs, plaster and/or chalk dust, a porous membrane, a fabric or knitted fabric, a nano- or microporous aluminum oxide layer. This can be influenced in terms of its properties, e.g. by varying the porous structure, such that it promotes the absorption of the liquid by capillary forces. It may, however, also be a material which is suitable for absorbing liquid in a different manner. According to this embodiment, the indicator substance initially lies in the frozen state on the barrier in the form of the material with a liquid-absorbing structure and cannot penetrate into it. In the liquid state and thus after exceeding the melting temperature of the indicator substance, the indicator substance located in the first sub-region diffuses slowly into the material which adjoins the first sub-region with a liquid-absorbing structure. As a result, the material is penetrated by indicator substance. The indicator substance reaches the second sub-region of the chamber in this manner in a delayed manner. The extent of the delay depends on the diffusion speed.

A further advantage is that the position of the diffusion front is a measure for the time which the indicator substance and thus also the sample in the receiving space were exposed to the inadmissible temperature range. This can be determined by determining the position of the diffusion front. The diffusion speed is indeed also a function of the viscosity which itself is temperature-dependent; it is, however, often sufficient to carry out an estimate between a few minutes and several hours up to days.

It is thus possible to detect both the exceeding of a threshold temperature as well as the duration of the exceeding. The basic principle of this embodiment thus lies in providing in or on the sample container a closed volume in which a frozen indicator substance is located on a material into which the indicator substance may diffuse slowly if the indicator substance, which is solid at the storage temperature, becomes liquid in the case of exceeding of the melting temperature.

A combination of several liquids with various melting temperatures and several diffusion sections which are combined or branch off is furthermore possible in order to thus be able to identify more precise indications of time in relation to the duration of the exceeding of the temperature.

According to one aspect of the invention, the indicator substance may be stored in a receptacle which tightly encloses the indicator substance in the liquid state, at least as long as the receptacle has not yet been destroyed, in particular for activation of temperature monitoring. The device for temperature monitoring may furthermore have an activation part which is guided movably in relation to the receptacle and which can be moved from a first position, referred to here as the starting position, into a second position, referred to here as the activation position. The movement into the activation position brings about that the activation part, as a result of mechanical pressure, destroys the receptacle at at least one point in particular in such a manner that the receptacle becomes permeable for the indicator substance in the liquid state. In other words, a mechanism is thus provided with which the device for temperature monitoring may be activated or switched into active mode at a desired point in time. The possibility for activation promotes trade and stock management since the liquid indicator substance cannot penetrate into the adjoining material with a liquid-absorbing structure up until activation.

The receptacle may be embodied as a plastic cushion which can be produced at particularly low cost. The receptacle may be embodied as a glass ball which, upon destruction, generates an audible crunching noise and thus acoustic feedback of activation.

The sample container may furthermore have a cover for closing off the receiving space, wherein the at least one chamber may be integrated into the cover. In this case, the cover may comprise a base body which can be pushed and/or screwed onto the sample container and which, in the screwed-on state, closes off the receiving space for receiving the biological sample. The base body may comprise an H-shaped cross-section. The base body may, for the formation of the at least one chamber, comprise a recess in which the receptacle with the indicator substance and the material with a liquid-absorbing structure are arranged. It was mentioned above that the device for temperature monitoring may comprise an activation part which is guided movably in relation to the receptacle. In this case, the activation part on the base body may be guided movably in the direction of the receptacle. The activation part may be arranged as a screw-in part on the base body. The activation part may comprise a projection which protrudes in the direction of the receptacle from the activation part, e.g. in the form or a tip or a thorn.

A further possibility of the realization according to the invention provides that the at least one chamber of the device is integrated into a base region of the sample container. In this case, a base region of the sample container may, for the formation of the at least one chamber, have a recess in which the receptacle with the indicator substance and the material with a liquid-absorbing structure are arranged. The recess may be closed off by a base part in which the activation part is guided movably. The base part may be embodied as a plastic cap. The base part may preferably have a machine-readable and/or optoelectronically readable code, in particular a barcode, a 2D code, a 2D barcode and/or a QR code.

A further variant provides that the activation position is fixed by a stop formed by the base part, up to which stop the activation part may be pushed into the base part. Moreover, the base part may be connected fixedly to the base region of the sample container, in particular be glued, melted, welded or otherwise fixed solidly to the base region of the sample container. The tamper-proofing of the temperature monitoring is improved as a result.

In the case of one advantageous variant, a surface of the material which adjoins the first sub-region comprises a covering. The covering is configured, in the case of cooling of the device to a storage temperature which lies below the melting temperature of the indicator substance, to undergo a transition from a first state of the covering, in which it is impermeable with respect to the indicator substance, irreversibly into a second state of the covering, in which it is permeable for the indicator substance. In the first state, the covering is impermeable, i.e. not porous, for the indicator substance even in the liquid state. The covering thus forms a separating layer. The covering may, for example, be a correspondingly configured membrane, a covering layer, a skin or a film or the like which only tears as a result of shrinking in the case of cooling to the storage temperature or otherwise becomes porous for liquids so that the indicator substance in the liquid state can pass via the opening formed by the at least one tear point or generally admission point from the first sub-region into the second sub-region.

This construction principle has the advantage that chambers already filled with indicator substance may be prefabricated and closed off. These can then be stored in ready made form and where necessary be cooled with the sample located in the sample container. Such chambers which serve as the indicator apparatus can therefore be stored in a premounted and filled form for as long as desired at room temperature since the covering is then not permeable.

A material which shrinks to a greater extent in the case of a reduction in temperature than the chamber material and as a result forms openings through which the liquid indicator substance can penetrate into the material with a liquid-absorbing structure is preferably used for this covering. In the case of correct storage, the indicator substance is frozen and thus cannot pass into the material or into the second sub-region of the chamber despite the openings which are present.

According to a further variant, the covering, e.g. in the form of a membrane, may be brought into the permeable second state by mechanical bending or pushing in. The covering may thus be made permeable for the indicator substance in the liquid state only shortly before use by bending or pushing in.

In the case of a further advantageous variant of this configuration, a structure and/or a composition of the material with a liquid-absorbing structure may be formed so that a diffusion speed of the indicator substance in the material reduces non-linearly with increasing distance from the first sub-region.

In this manner, very short periods of time (seconds up to minutes) spent at excessive temperature in the upper region of the material, i.e. the part of the material which faces the first sub-region, and very long periods (hours to days) spent in the lower region, i.e. the part of the material which faces away from the first sub-region, may be proven.

A further advantageous embodiment of the invention provides that the barrier is a separating element which is permeable in relation to the indicator substance in the liquid state and which is arranged between the first and second sub-region. The barrier thus forms a separating layer between first and second sub-region which is only permeable for the indicator substance in the liquid state, but not in the frozen state. The separating element which is permeable in relation to the indicator substance in the liquid state may be embodied as a porous separating wall, membrane, film, skin or capillary system.

One possibility of the realization according to the invention provides in this case that the separating element is configured, in the case of cooling of the device to a storage temperature which lies below the melting temperature of the indicator substance, to tear at at least one point as a result of thermal contraction so that the indicator substance may pass in the liquid state via the opening formed by the at least one tear point from the first sub-region into the second sub-region.

This variant has in turn the advantage that such chambers which serve as an indicator apparatus may be stored in a premounted manner and filled manner for as long as desired at room temperature since the separating element is then not permeable. Where necessary, the chamber may then be arranged on the sample container and cooled with the sample located in the sample container, wherein the at least one tear point is then formed. In the case of correct storage, the indicator substance is frozen and can thus not pass into the material or into the second sub-region of the chamber despite the openings which are present.

The separating element may have at least one predetermined breaking point at which the separating element tears during cooling of the device to the storage temperature. A predetermined breaking point within this meaning is a given point of the separating element at which the separating element tears during cooling to storage temperature. This has the advantage that the position and size of the tear point are predetermined and thus also the throughflow rate of the indicator substance enabled as a result if the indicator substance is liquid.

Predetermined breaking points may be realized, for example, by thinned sections of the separating element at specific points, for example, in the form of punctiform thinned sections at the edge of the separating layer or in the form of lines running crosswise over the separating layer.

Such separating layers could be produced, for example, using the injection molding process. Alternatively, the material may also be configured so that it tears in an irregular manner.

A further advantageous variant of the embodiment comprising the separating element provides that a gas is present in the second sub-region. Instead of the gas, a substance may also be present in the second sub-region, which substance has a lower melting point than the indicator substance. The substance may thus also be a material which is also liquid at the storage temperature or at least prior to the liquefying of the indicator substance.

The period of time of the unauthorized increase in temperature may be determined on the basis of the change of a property of the gas or the substance, e.g. on the basis of its color, transparency, optical angle of rotation, impedance, etc. which results from mixing with the indicator substance which enters into the second sub-region. Since this process is configured to be non-reversible in the connected volume, the device for temperature monitoring formed in this manner can be regarded as tamper-proof and manipulation-proof.

It is furthermore possible in the context of the invention that an outer wall of the chamber comprises a closable opening to the first sub-region, for filling of the first sub-region with an indicator substance. The opening may be welded, closed off with a further substance or otherwise sealed off after filling with the indicator substance.

The at least one chamber may be formed by a container with one or more cavities which can be and/or is/are arranged on the outside of the sample container. The term "can be and/or is/are arranged" should comprise "can be and/or is/are fastened", "be and/or is/are coupled", "can be and/or is/are connected". The container for the formation of the at least one chamber which is partially filled with indicator substance may thus be differentiated from the sample container.

In this case, the container can be capable of being arranged and/or be arranged on the outside of the container or inside the container. One possibility of the realization according to the invention provides that the container for the formation of the at least one chamber is fastened detachably to the sample container. A detachable fastening should also encompass in particular a sliding or pushing of the container onto the sample container. This has the advantage that the container may be stored and prepared (e.g. filling with the indicator substance) spatially separate from the sample container.

For example, the sample container may comprise a cover for closing off the receiving space. According to one preferred exemplary embodiment, the at least one chamber may be integrated into the cover, e.g. into the head part and/or the shaft of the cover. For example, the cover may comprise a shaft which is in engagement with an upper end region of the receiving space of the sample container, wherein the at least one chamber is integrated into the shaft.

The arrangement of the at least one chamber in the cover has the particular advantage that no additional installation space is required outside the sample container. A further advantage is that the at least one chamber which serves as an indicator apparatus may be stored and prepared (e.g. filling the chamber with the indicator substance and freezing the indicator substance) together with the cover spatially separate from the rest of the sample container. An integration of the chamber into the shaft of the cover is particularly advantageous. According to this variant, the shaft of the cover comprises a cavity which is partially filled with indicator substance. Particularly in the case of cryogenic tubes, often only a lower sub-volume of the receiving space is filled with the biosample so that an upper sub-volume may be used for the arrangement of the indicator substance.

A further possibility of the realization according to the invention provides that the at least one chamber is formed by a container and that there is fastened to an outer wall of the sample container a receiver, for example, a sleeve or insertion pocket into which the container may be inserted and/or is inserted for retention on the sample container.

According to a further advantageous embodiment, the at least one chamber may be formed by a double-walled push-on part which can be pushed or slid onto an outer shell surface of the sample container and at least partially engages around it in the pushed-on state. This variant is particularly advantageous for cylindrical sample containers, in particular cryogenic tubes. The double-walled push-on part may be embodied as a hollow cylinder or partial hollow cylinder, the inner diameter of which corresponds to the outer diameter of the sample container so that the push-on part engages around the cylindrical sample container in the manner of a cuff or clamp.

The sample container may furthermore be glued, melted or fixed solidly in another manner to the push-on part. As a result, a removal of the push-on part for manipulation purposes, e.g. to replace a push-on part which exhibits undesirable heating with a new push-on part, can be prevented.

The sample container may, however, also be a bag known per se for the storage and/or cryogenic storage of blood samples or stem cells which is retained in a cassette. The at least one chamber may be formed by a container which is fastened to an outer side of the bag or which is fastened to the cassette. The at least one chamber may also be formed by a container which is present floating freely in the interior of the bag. The container with the indicator substance may in this case be calibrated in terms of density so that it floats centrally in the bag liquid and detects the core temperature of the bag there.

According to a further preferred embodiment, the device may comprise a plurality of chambers which are in each case only partially filled with an indicator substance, the melting temperature of which lies in a range from −20° C. to −140° C., and comprise a barrier, as was described above. For example, a container may comprise, for the formation of several chambers, several sub-cavities formed by separating walls. In this case, each sub-cavity forms a chamber which contains the indicator substance and the barrier. The indicator substances in the chambers may have different melting temperatures. Various temperature threshold values can thus be monitored, wherein each indicator substance is selected and/or its mixture ratio is/are adjusted so that their melting point corresponds to one of the temperature threshold values to be monitored. This embodiment has the advantage that the achieved temperature intervals which the sample has reached can be restricted more precisely.

According to a further embodiment of the invention, the at least one chamber may be integrated into the sample container itself, i.e. the sample container itself can have in its interior such a chamber or several chambers. As a result, a separate component arranged on the outside of the sample container for the formation of at least one chamber may be dispensed with. For example, the receiving space of the sample container for the formation of the at least one chamber may be embodied to be double-walled with an inner wall and an outer wall, wherein an intermediate space between the inner wall and the outer wall is partially filled with the indicator substance. For the formation of several chambers, the intermediate space may be divided by separating walls into sub-spaces.

According to one preferred embodiment, the device may have a measuring apparatus which is formed to detect the presence of the indicator substance in the second sub-region of the chamber and/or a fill level of the indicator substance in the first and/or the second sub-region of the chamber. The measuring apparatus may merely by way of example be an optical or optical-electric measuring apparatus in order to determine a change in configuration of the indicator substance e.g. with an optical transmission, scattered light or reflection measurement.

According to a second aspect of the invention, the stated objects are achieved by a method for temperature monitoring of cryopreserved samples which uses a device for temperature monitoring, as described in this document. The embodiments relating to the device, in particular its advantageous embodiment variants, should thus, in order to avoid repetition, also be regarded as disclosed according to the method and capable of being claimed as such.

A substance, the melting temperature of which corresponds to a predetermined threshold temperature, the exceeding of which should be monitored, may preferably in turn be selected as the indicator substance.

According to the method, a device for temperature monitoring, as described in this document, may thus be provided, wherein the device contains at least one indicator substance in the frozen state in the first sub-region of the chamber. The receiving space of the sample container contains a cryopreserved biological sample. The method further comprises cooled storage of the device for cryopreservation. The method further comprises checking whether indicator substance is located at a later point in time in the second sub-region of the chamber.

If this is the case, an exceeding of the melting temperature of the indicator substance and thus the threshold temperature to be monitored can be concluded, in particular also when the exceeding has only occurred briefly.

One particular advantage of the invention lies in the fact that the presence of indicator substance in the second sub-region directly displays that the cryogenic sample has heated above a definable threshold temperature, even if only briefly. This can be quickly and easily determined by visual inspection or also in a technically automated manner by means of a correspondingly configured measuring apparatus without the sample having to be removed from the sample container or thawed out.

According to one advantageous further development of the method, a parameter can furthermore be determined which indicates a measure of the quantity of indicator substance which has moved into the second sub-region of the chamber and/or a measure of the quantity of indicator substance located in the first sub-region of the chamber. Such a parameter indicates a measure for the duration which the sample has spent above the threshold temperature.

A parameter is, for example, a variable which indicates the quantity of indicator substance in the first or in the second sub-region. The parameter may be the fill level of the indicator substance in the second sub-region or the length of the diffusion section which the indicator substance in the material with the liquid-absorbing structure has reached.

According to one particularly preferred embodiment of the method, a device for temperature monitoring is used to carry out the method, which device has either a separating element or a covering which only becomes permeable for the indicator substance in the liquid state during cooling. It was already described above that there may be arranged between the first and second sub-region a separating element which is configured, in the case of cooling of the device to a storage temperature which lies below the melting temperature of the indicator substance, to tear as a result of the thermal contraction at at least one point so that the indicator substance in the liquid state can pass via the opening formed by the at least one tear point from the first sub-region into the second sub-region.

It was also described that a surface of the material adjoining the first sub-region may comprise a covering, e.g. a membrane or covering layer, which is configured, in the case of cooling of the device to a storage temperature which lies below the melting temperature of the indicator substance, to undergo a transition from a first state of the covering, in which it is impermeable with respect to the indicator substance, irreversibly into a second state of the covering, in which it is permeable for the indicator substance.

According to the particularly preferred embodiment of the method, at least one of the following test steps can be carried out in order to check the functionality of the device for temperature monitoring, in particular the functioning capacity of the indicator apparatus:

Firstly, it may first be tested whether the second sub-region of the at least one chamber is free from indicator substance after filling of the first sub-region with indicator substance and prior to freezing of the indicator substance. In this state, the separating element which serves as a barrier should still be intact so that no indicator substance could be present in the second sub-region located below the first sub-region. If, however, this is the case, the chamber cannot be used since it is already defective. The same applies to the case if a chamber with a covering is used instead of a chamber with a separating element.

Secondly, it may be tested whether the second sub-region of the at least one chamber is free from indicator substance after freezing of the indicator substance located in the first sub-region of the at least one chamber and prior to cooled storage of the device for cryopreservation. After cooling of the device to storage temperature or at least below the melting temperature of the indicator substance and the temperature at which the separating element should tear, the separating element should be ripped and the indicator substance frozen so that in turn no indicator substance should be in the lower second sub-region. If this is not the case, a new chamber should be used. The same applies in turn in the case that a chamber with a covering is used instead of a chamber with a separating element.

Thirdly, it may be tested, if a cryopreserved sample is removed for use and if no indicator substance is then located in the second sub-region of the chamber, whether the covering has correctly transferred into the permeable second state or whether the separating element or the covering of the at least one chamber is correctly torn. It could namely be the case that the separating element or the covering is not torn and thus the exceeding of the melting temperature of the indicator substance was not displayed. This can be tested, for example, in that the relevant chamber with indicator substance is left to lie for a certain time after thawing. The sample can in the mean time already undergo further processing. If the separating element or the covering was correctly torn and the storage temperature was below the melting temperature of the indicator substance for the whole time, the indicator liquid will in any event pass through the barrier into the second sub-region at room temperature.

All of these testing steps are preferably carried out in the framework of a temperature monitoring of a cryopreserved sample. In this manner, the functioning capacity of the chamber may be proven and it can clearly demonstrated that the storage temperature has matched the requirements over the entire time.

The term sample container refers in particular to a container which is configured for cryopreservation. The sample container is preferably produced using low-temperature-compatible plastic material for temperatures below −140° C. The plastic material can tolerate repeated temperature changes without change and without damage. A plastic material is preferably used, the water absorbing capacity of which is <1% of the net mass, in particular <0.1% of the net mass. Cryogenic storage elements according to the invention are based, for example, on polyurethane or polyethylene.

The term "biological sample", also referred to in abbreviation as sample in this document, refers to biological material such as cells, tissue, cell components, biological macromolecules, etc. which are subjected to cryopreservation in the sample container, where applicable, in a suspension and/or in combination with a substrate material. A substrate which is configured for adherent receiving of biological cells which are part of the biological sample may thus be arranged in the receiving space.

BRIEF DESCRIPTION OF THE DRAWINGS

The preferred embodiments and features of the invention described above may be combined with one another. Further details and advantages of the invention are described below with reference to the enclosed drawings. In the drawings:

FIG. 9 shows a mixability matrix of solvents;

FIG. 11 shows an exemplary embodiment of a device for temperature monitoring, and FIG. 12 shows an exemplary embodiment of a device for temperature monitoring.

DETAILED DESCRIPTION OF PREFERRED EMBODIMENTS

Figure 1:
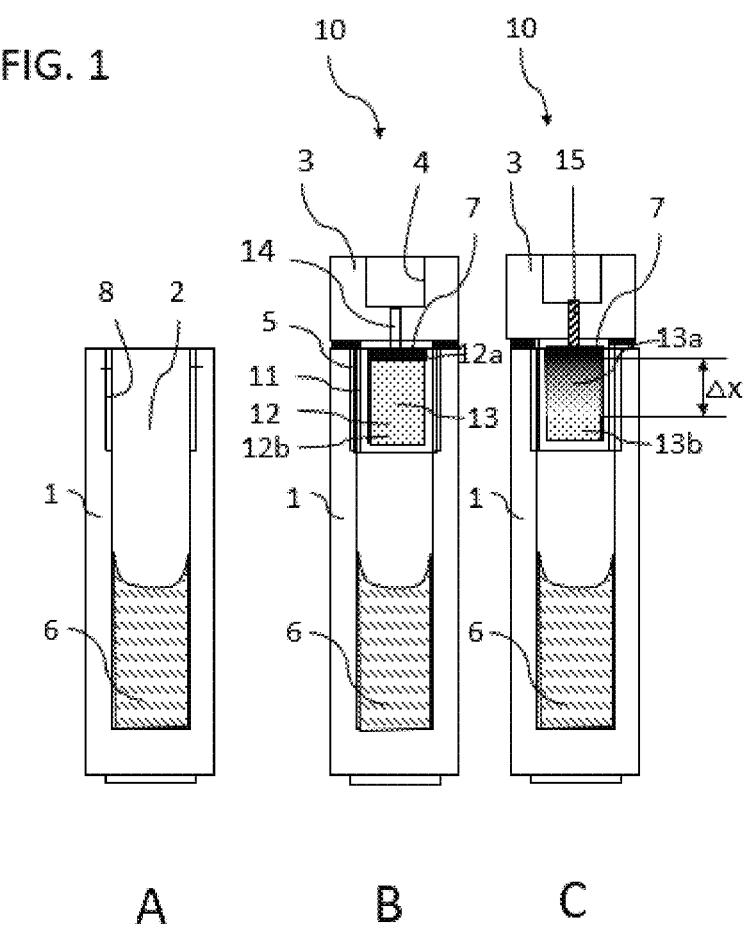
FIGS. 1-4 show schematic views of various exemplary embodiments of a device for temperature monitoring of a cryopreserved biological sample.

Identical elements or functionally equivalent elements are designated by the same reference numbers in all the figures and are partially not described separately.

FIG. 1A shows by way of example a cryogenic tube 1, representative of other cryogenic sample containers, such as straws, bags, boxes etc.

The cryogenic tube comprises a receiving volume 2 for the biosample in which the biomaterials are located. The biosample here is a cell suspension 6. The cryogenic tube is shown in FIG. 1A still without a screw cover closure. The cryogenic tube further comprises a cover 3, shown in FIG. 1B, which closes off the vessel and at the top has an engagement 4 via which cover 3 can be turned with a tool (not shown) in the case of automation. These cryogenic tubes 1 may also contain a base into which a barcode square or another mark is optionally inserted. In this form, usually standing perpendicular in receivers, cryogenic tubes 1 are stored in the low-temperature containers.

The storage-ready system is represented in FIG. 1B. The cover has a head part which sits on receiving volume 2 and a shaft 5 formed thereon which engages into receiving volume 2 in the screwed state. The corresponding region of receiving volume 2 has a thread 8. A chamber 11 which forms a self-enclosed volume 12 is integrated into screw cover 3. Inner volume 12 of chamber 11 is represented in FIG. 1B by the black and dotted region.

A material 13 which is porous or otherwise suitable for absorbing a liquid and above it a small cavity (first sub-region) 12a, which is filled with indicator substance 7 via a small opening 14, are located in this volume 12 in a second sub-region 12b. Indicator substance 7 becomes solid in the case of undershooting of the desired threshold temperature, e.g. −70° C., and becomes liquid again in the case of exceeding.

Via the selection of suitable liquids and the mixture ratio of liquids, their melting point may be set at a desired value in a range from −20° C. to −140° C. and thus a suitable indicator substance 7 may be selected according to the threshold temperature to be monitored, which is explained in greater detail below in conjunction with FIGS. 6 to 9.

Filling of first sub-region 12a is expediently carried out during cooling, shortly before setting of the storage temperature of cryogenic tube 1, i.e. generally below −140° C., so that indicator substance 7 does not have sufficient time to penetrate into material 13, which can be minutes, hours or days depending on the design.

At the storage temperature, indicator substance 7 is then solid so that nothing changes any more in the arrangement as represented in FIG. 1B. Opening 14 is welded, closed off with a substance 15 or otherwise sealed off.

Device 10 formed in this manner composed of sample container 1 with integrated chamber 11 is configured for temperature monitoring of a cryopreserved biological sample 6. FIG. 1B shows the device in an initial state and in a state where no interim exceeding of the melting temperature of indicator substance 7 has taken place. FIG. 1C shows the device in a state if an interim exceeding of the melting temperature of indicator substance 7 has taken place.

If sample 6 has thus been heated at any point in time above the melting temperature of the indicator substance 7, for example a dyed alcohol/water mixture with a melting temperature of −70° C., now liquid indicator substance 7 then penetrates into material 13, as a result of which a state of device 10, as represented in FIG. 1C, is produced. FIG. 1C shows a state in which the indicator substance has already diffused into an upper region 13a of length Δx of material 13, but has not yet reached lower region 13b.

The distance (diffusion section) Δx is a measure for the duration which sample 6 has spent above the threshold temperature. Since this process cannot be made reversible, the system is tamper-proof as long as entire screw closure 3 is not replaced, which can nevertheless be detected by way of markings, codes, etc. and thus prevented.

The structure of such a chamber 11 can thus be varied in various ways. For example, in one case, porous material 13 may be covered with a covering (not represented), e.g. a thin skin or membrane, which only tears as a result of shrinking in the case of cooling to the storage temperature or otherwise becomes permeable for indicator substance 7 in the liquid state. This construction principle has the advantage that the prefilled cover can be stored in a premanufactured, closed and prefabricated manner and like the previously normal covers can only be screwed on and cooled with sample 6 and sample container 1 in the event of use.

A material, which shrinks to a greater extent in the case of reduction of the temperature than the cover material and as a result forms openings through which indicator substance 7 in the liquid state can penetrate into material 13, may suitably be used for this covering. In the case of correct storage, indicator substance 7 is frozen and may thus not pass into material 13 or into second sub-region 12b despite the openings which are present.

Variation possibilities furthermore emerge via the structure and the design of material 13. This material may be influenced in terms of properties so that it promotes the absorption of the liquid as a result of capillary forces or a desired diffusion speed is also set which reduces non-linearly with the distance, but in a familiar manner downwards. In this manner, very short periods of time (second up to minutes) spent at excessive temperature in the upper region and very long periods (hours to days) spent in the lower region of material 13 can be proven.

An intermediate layer which can be made permeable from the outside shortly prior to use by bending or pushing in may also be used as a covering.

Figure 2:
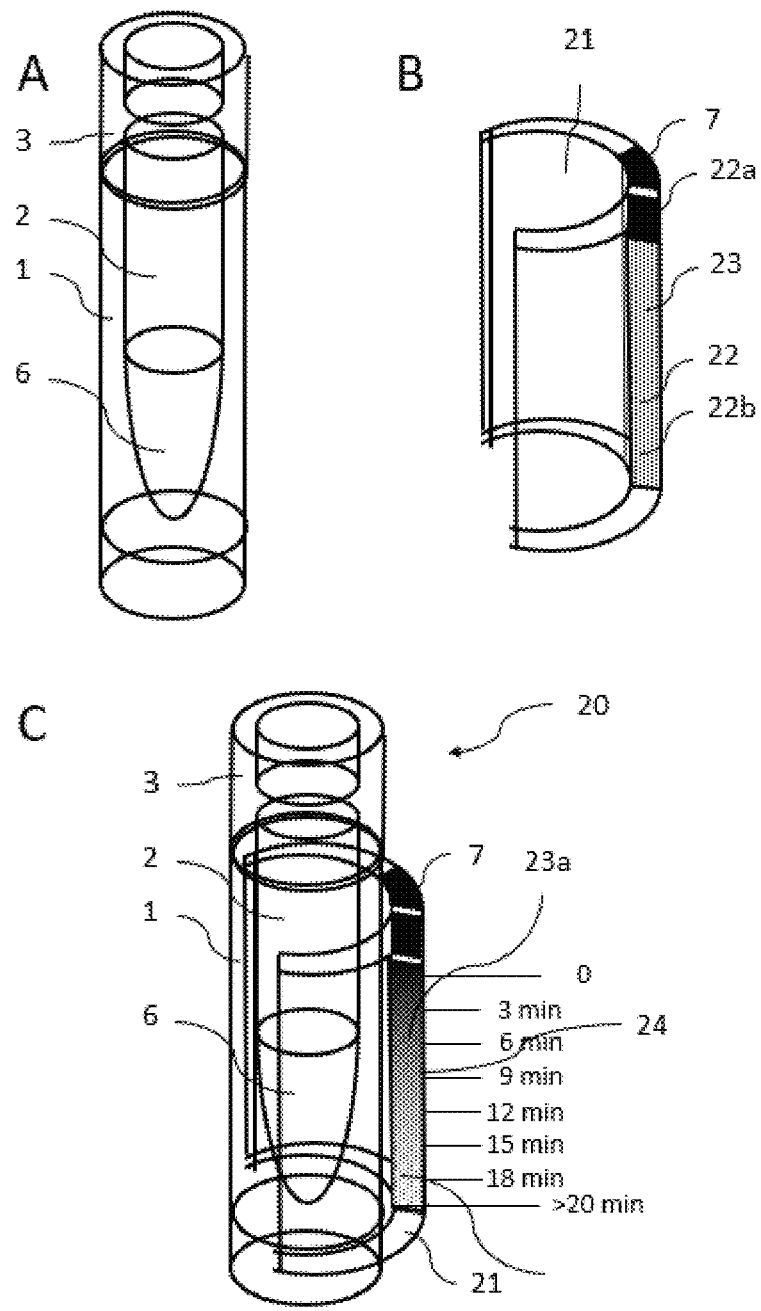

Views A, B and C of FIG. 2 illustrate a further configuration of the invention, wherein FIG. 2C shows a device 20 for temperature monitoring of a cryopreserved biological sample in a state after an interim exceeding of the melting temperature of indicator substance 7 has taken place.

FIG. 2A initially shows a cryogenic tube 1 which is completely closed off with a cover 3, as is normally used in cryobanks. FIG. 2B shows a push-on part 21 which is embodied to be double-walled, which is composed of plastic and which can be placed on the outer shell surface of cryogenic tube 1, as represented in FIG. 2C.

One or more volumes 22, in which in each case an indicator substance 7 in the frozen state on a porous medium 23 is located in an upper sub-region 22a, is/are located in this plastic part 21 in an analogous manner to the exemplary embodiment illustrated in FIG. 1 in a perpendicular alignment. The porous medium is located in lower sub-region 22b of volume 22. Plastic part 21 may thus form a chamber according to the invention or also several if inner volume 22 of the plastic part is divided by separating walls into several sub-volumes which in each case have an indicator substance and a porous medium.

In an analogous manner to the exemplary embodiment illustrated in FIG. 1, indicator substance 7 only diffuses into material 13 located therebelow if a melting temperature of indicator substance 7 was exceeded and indicator substance 7 melts.

FIG. 2C shows a state in which the indicator substance has already diffused into an upper region 23a of porous medium 23.

The diffusion section in the case of this embodiment is a few millimeters up to more than ten centimeters depending on the size and geometry of sample container 1. Plastic part 21 can be provided with a scale 24 which enables more precise recording of times.

Alternative embodiments are furthermore sleeves or cylinder parts which can be pushed onto cryogenic tube 1 in a similar manner. In order to prevent tampering, the attachment part can be glued, melted on or fixed solidly in another manner.

Figure 3:
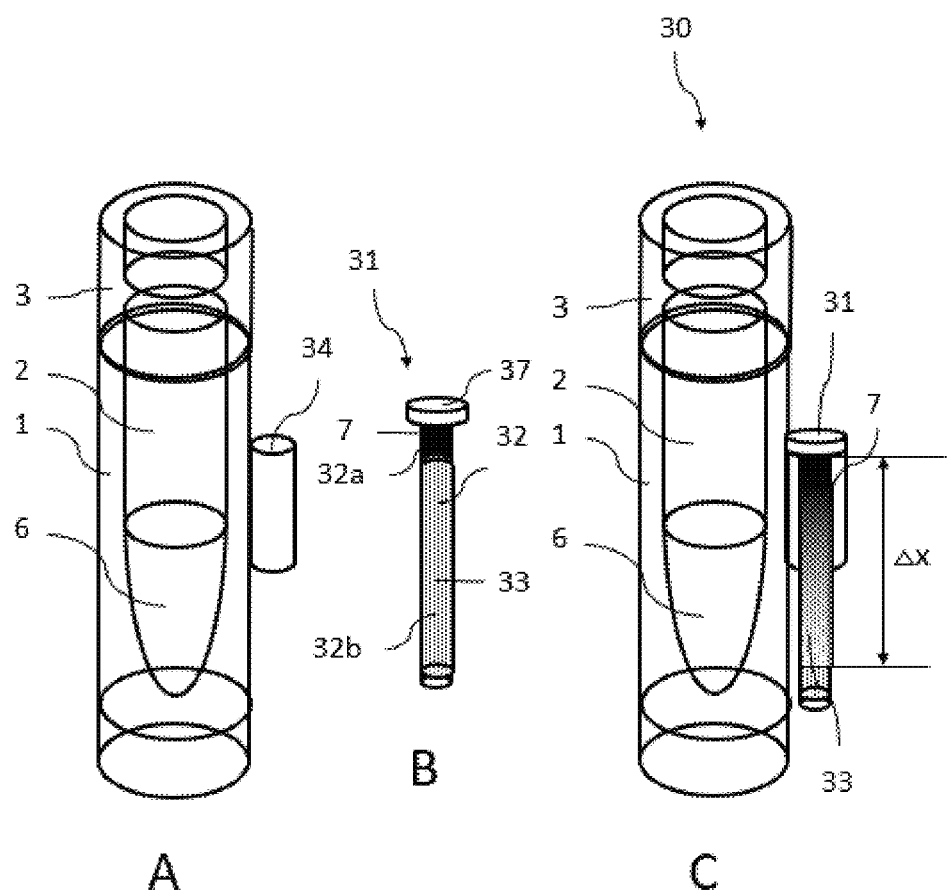

Views A, B and C of FIG. 3 illustrate a further configuration of the invention, wherein FIG. 3C shows a device 30 for temperature monitoring of a cryopreserved biological sample in a state after an interim exceeding of the melting temperature of indicator substance 7 has taken place.

FIG. 3A again shows a cryogenic tube 1 which is completely closed off with a cover 3. In contrast to the cryogenic tube shown in FIG. 2A, a receiver 34 into which a container 31 represented in FIG. 3B is pushed is fastened to a lateral outer surface of cryogenic tube 1. This container 31 forms a cylindrical or differently shaped inner volume 32. The container is secured from falling out of receiver 34 by way of a disc 37. There is located in a first sub-region 32a of inner volume 32 indicator substance 7, optionally on a separating layer (not represented), which only becomes permeable for the indicator substance in the liquid state in the event of cooling to storage temperature, and thereunder in a second sub-region 32b porous absorbent material 33. In the case of a porous material with a strong capillary action, the position of the unit plays a subordinate role. A vertical arrangement and storage of the sample is, however, recommended.

FIG. 3C shows device 30 formed from cryogenic tube and container 31 for temperature monitoring in a state after an interim exceeding of the melting temperature of indicator substance 7 has taken place. It is apparent that, in contrast to the state of the container shown in FIG. 3B, the indicator substance has diffused into porous material 33. Δx again indicates the length of the diffusion section.

Figure 4:
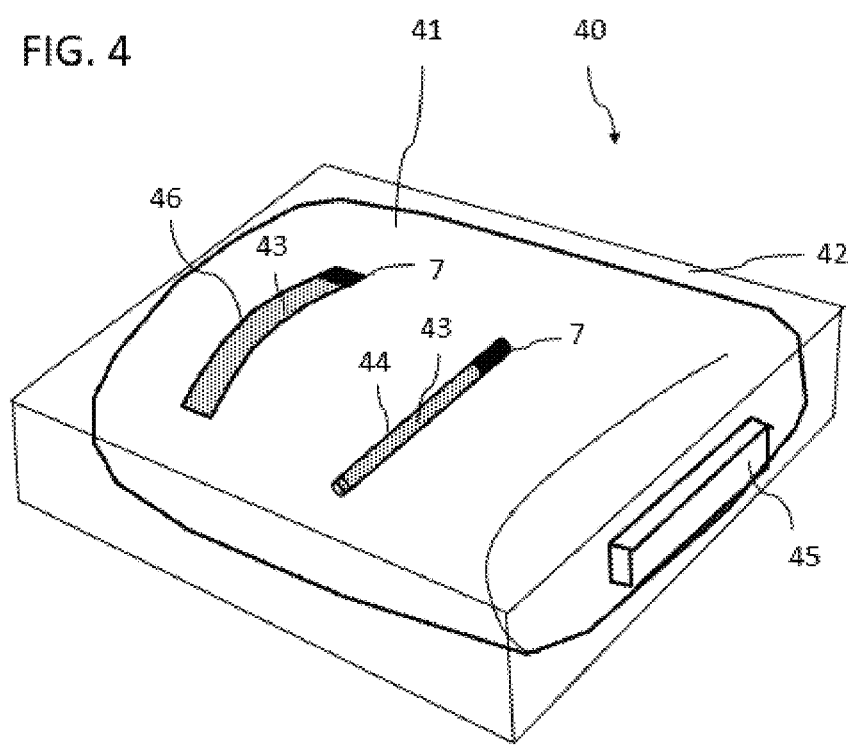

FIG. 4 shows a bag 41 as is used for the storage of stem cells and blood samples. These bags are often still found in a cassette 42 which is composed of aluminum. A device 40 for temperature monitoring of a cryopreserved biological sample can in turn be formed from the sample container in the form of bag 41 and a temperature-sensitive system. The temperature-sensitive system is formed in an analogous manner to chambers or containers 11, 21, 31 of FIGS. 1 to 3 in turn by a container 44, 45 or 46 which is only partially filled with an indicator substance 7. The container further has a porous material 43 which brings about that, if indicator substance 7 is located in a first sub-region of the chamber in the liquid state, this indicator substance 7 passes into a second sub-region of the container in a delayed manner.

Container 43 can thus be fitted on bag 41 on an outer side of the bag. Container 45 can also be fitted on the outside or inside of cassette 42. Container can also be fitted floating freely and fixed in the interior of bag 41. The variant on the inside requires sterilization and inert materials on the outside. This system may be calibrated in terms of density so that it floats centrally in the bag liquid and records the core temperature of the bag there.

Figure 5:
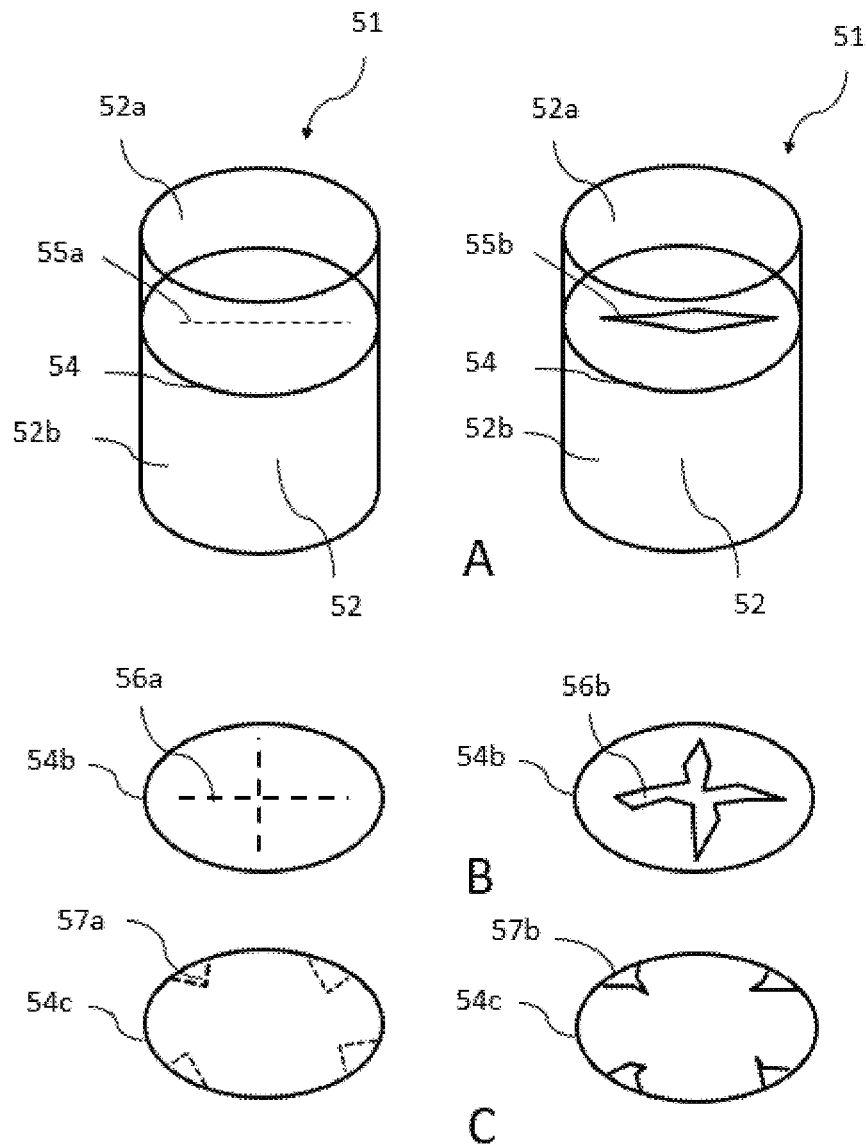
FIG. 5 shows schematically different embodiment variants of a chamber with a separating element as a barrier.

FIG. 5 schematically illustrates various embodiment variants of a chamber or a container which are configured as the indicator apparatus for temperature monitoring.

FIG. 5A shows a container 51, for example, a cylinder, which in its inner space 52 forms two sub-volumes 52a and 52b which are separated by a barrier 54. An indicator substance (not represented) is incorporated in upper sub-volume 52a. Barrier 54 may be a membrane or film which has predetermined breaking points, schematically represented by dashed line 55a, at which this barrier 54 tears in the case of cooling to the storage temperature. The barrier is configured so that it only tears at a temperature below the melting temperature of the indicator substance which is located in sub-volume 52a. In this manner, initially only upper sub-volume 52 can be filled with liquid indicator substance and subsequently cooled.

Barrier 54 may also be composed of a material which shrinks to a greater extent in the event of cooling than the cylinder material and therefore tears to a more or less irregular extent.

Container 51 filled with indicator substance may then be arranged on a sample container, in which a cryogenic sample is stored, and cooled together with it to storage temperature which lies below the melting temperature of the indicator substance.

In the case of cooling, the barrier tears so that the indicator substance located in sub-volume 52a in the liquid state can pass via opening 55b formed by the at least one tear point slowly from first sub-region 52a into second sub-region 52b.

FIG. 5B and FIG. 5C respectively show further embodiments of a barrier 54b and 54c respectively with such a predetermined breaking point 56a or 57a respectively. In each case the predetermined breaking points in the case of an intact barrier prior to cooling are represented on the left in FIGS. 5B and 5C, on the right torn open after cooling (openings 56b or 57b).

As long as the test liquid remains frozen in upper sub-volume 52a, no passage occurs through opening 55b, 56b or 57b into volume 52b. In the case of correct storage, the filling appears separate as before freezing and can be checked as often as desired at the storage temperature. If such a sample is thawed out, the phase in upper sub-volume 52a becomes liquid and penetrates via opening 55b, 56b or 57b into volume 52b. In this manner, it is possible to test whether barrier 54 was correctly torn at the storage temperature, therefore the system functioned in the desired manner.

By way of the variants shown in FIGS. 1 to 5, more complex systems with various such elements and temperature recordings or mixtures of two or more liquids during heating may thus be built up.

Figure 6:
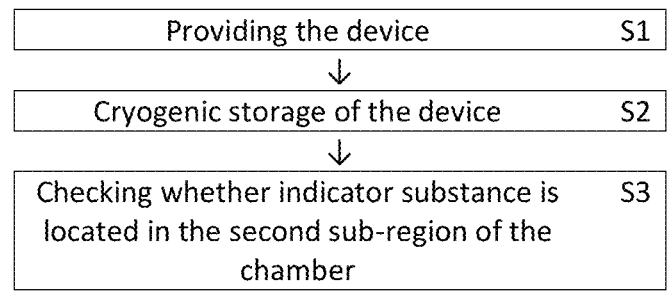
FIG. 6 shows a flow chart to illustrate an exemplary embodiment of a method for temperature monitoring of a cryopreserved biological sample.

FIG. 6 illustrates on the basis of a flow chart a method for temperature monitoring of a cryopreserved biological sample. In step S1, a device according to the invention for temperature monitoring is provided, for example, one of devices 10, 20, 30, or 40. In this case, depending on the temperature threshold value which is supposed to be monitored in the case of cryogenic storage, a suitable liquid or a liquid mixture is to be selected as indicator substance 7.

Via the selection of suitable liquids and the mixture ratio of liquids, their melting point can be set to a desired value in a range from −20° C. to −140° C.

Figure 7A:
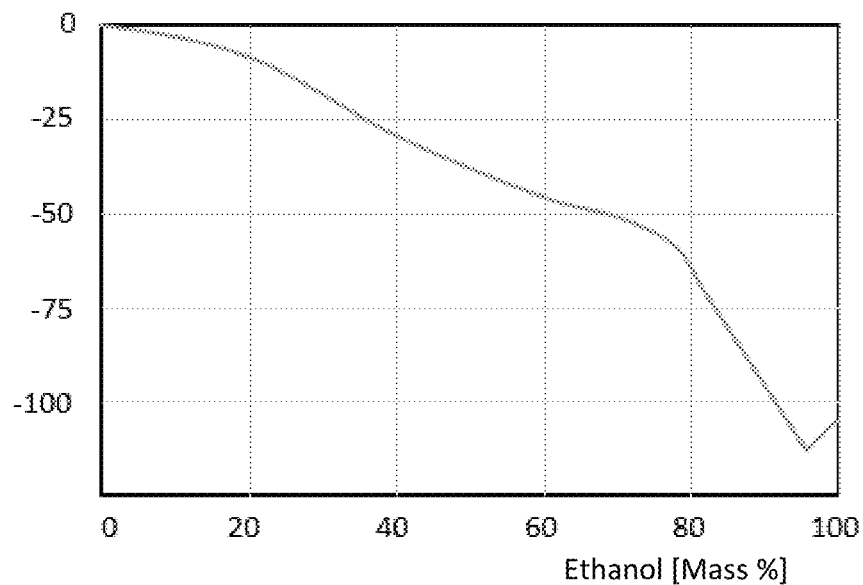
FIGS. 7A, 7B, 8A show in each case a melting diagram of a liquid mixture.
Figure 7B:
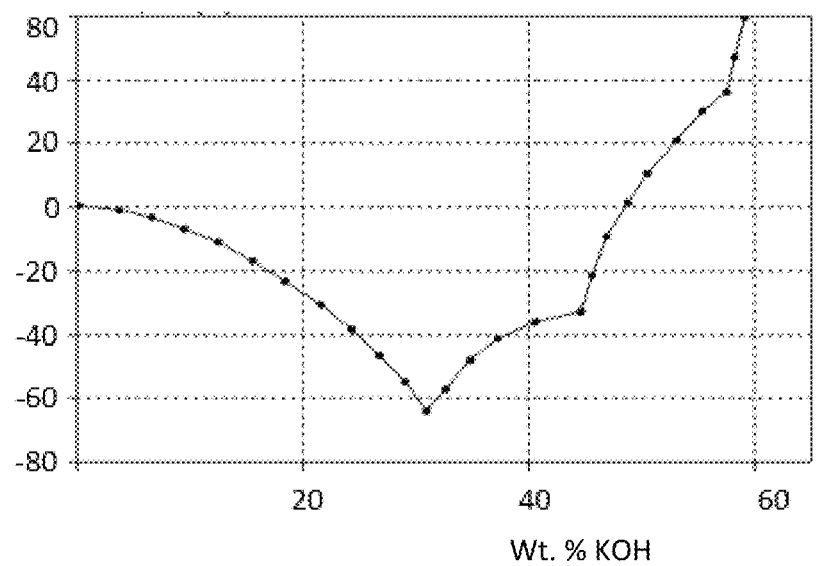
Figures 8A, 8B:
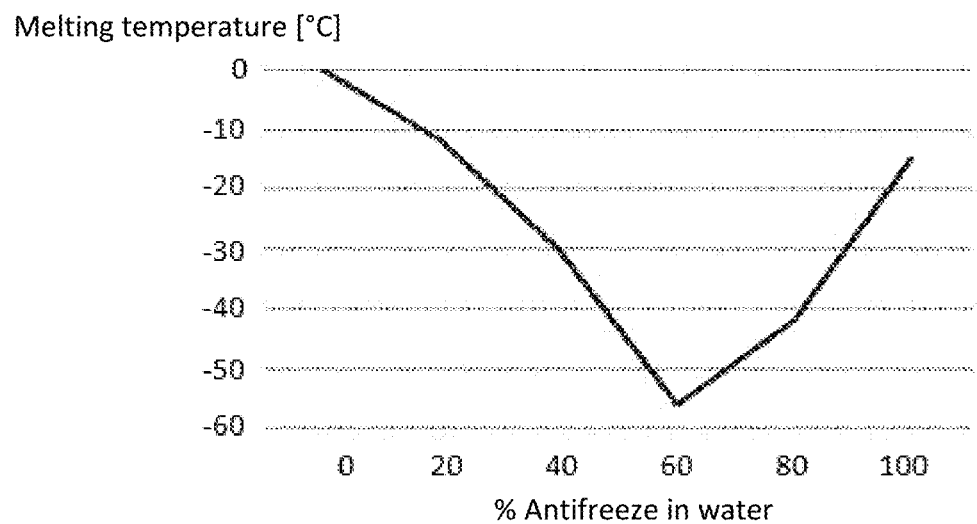
FIG. 8B shows a table with melting points of a number of pure liquids.
Figure 9:
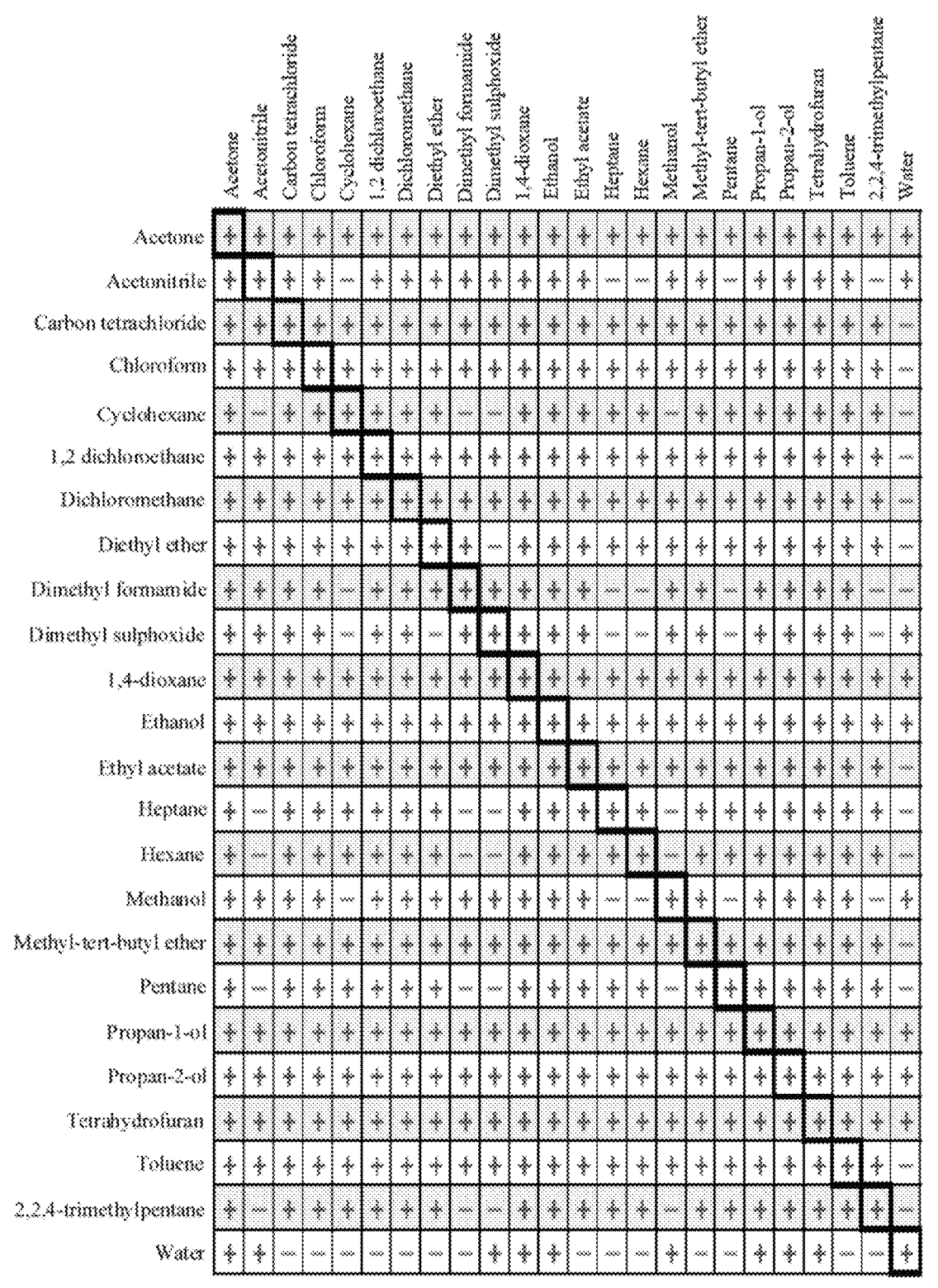

By way of example, FIG. 7A indicates the profile of the melting point as a function of the mixture ratio of an alcohol and water, with which, in the case of a moderate increase in viscosity with falling temperature, a temperature range between 0° C. and −118° C. can be covered. Should e.g. a temperature threshold value of −118° C. be monitored, the ethanol ratio can be set at 93.5%. Melting points up to a value of slightly below −60° C. can also be set by adding potassium hydroxide (KOH) to water, which is shown in FIG. 7B on the basis of a melting diagram. A mixture of water and antifreeze can also be used as the indicator substance, which is illustrated by the melting diagram of FIG. 8A. The table of FIG. 8B lists freezing points/melting points of further pure liquids which can be used on their own or as a mixture with another liquid as the indicator substance. Further liquid mixtures which are suitable as the indicator substance include chloroform/cyclohexane mixtures or other mixable liquids which can be inferred e.g. from the mixability matrix of solvents of FIG. 9.

Liquids and plastic materials with good wettability and low viscosity at low temperatures are primarily selected in order to configure the change in position to be as extensive as possible and the additional compartment as small as possible.

If several temperature threshold values are supposed to be monitored during cryogenic storage or if the achieved temperature intervals which the sample reaches should be restricted more precisely, several different indicator substances with different melting points can correspondingly be used which are then fitted in different chambers in or on the sample container.

The indicator substance may, depending on the embodiment of the device, be cooled jointly with or separately from the device and transferred into a frozen state, as was described by way of example above in the context of the figures.

In step S2, the device with a cryogenic sample in the receiving space of the sample container is stored at a storage temperature below the melting temperature.

It is subsequently possible to check by means of the indicator substance at any desired point in time during the storage process whether an undesirable, if only temporary heating of the cryogenic sample has taken place (step S3). To this end, it is checked whether indicator substance is located in the second sub-region of the chamber at a later point in time. If this is the case, it can be concluded that the melting temperature of the indicator substance and thus the threshold temperature to be monitored have been exceeded, in particular even if the exceeding has only occurred for a short time.

A control process is described below which is suitable for a device for temperature monitoring which has a separating element as a barrier or a covering as part of the barrier in the chamber which tears as a result of the thermal shrinking and thus forms the openings for the penetration of the indicator liquid into the second sub-region of the chamber.

The control process described below makes it possible in the case of each sample to check the functionality of the device, in particular the chamber which serves as the indicator apparatus.

In a first test step, the indicator apparatus in the form of the chamber with the barrier at room temperature can be viewed before the sample is frozen. The indicator substance is then located in the liquid state on one side of the barrier, i.e. in the first sub-region of the chamber, the barrier is intact, and no indicator substance is located in the second sub-region located thereunder. If this is not the case, this chamber cannot be used since it is already defective. If the chamber is, for example, integrated into the cover, it can no longer be used and is replaced with another one.

After cooling below the melting temperature of the indicator substance, the barrier should be opened by the thermal contraction, e.g. at preweakened points, but the indicator liquid is frozen so that the image must correspond to that prior to freezing. This can be checked in a second test step. If this is not the case, a new chamber, e.g. a new cover, should be used.

In the deep-frozen state, it is thus possible to check at any desired points in time whether an increase in temperature above the melting point of the indicator substance has taken place. This should then have passed through the barrier into the second sub-region. This is readily apparent in a third test step in particular if the indicator substance contains a dye as the indicator additive.

If one removes a deep-frozen sample for use which has not experienced any exceeding of the melting temperature of the indicator substance, the state of the chamber has the same appearance as described under the first two test steps, i.e. no indicator substance is located in the second sub-region of the chamber. It could nevertheless be the case that the separating element is not torn at all and the barrier has thus not become permeable and thus the exceeding of the indicator substance melting temperature was not displayed. This can be tested in that the chamber is left to lie for a certain time after thawing out. For example, in the case of a chamber integrated into the cover, only the cover can be left to lie, while the sample can be further processed. If the separating element was correctly torn and the temperature was below the melting temperature for the whole time, the indicator liquid will in any event pass through the barrier into the test volume, i.e. into the second sub-region, at room temperature. In this manner, the functioning capacity of the indicator apparatus is proven and it is clearly demonstrated that the storage temperature has matched the requirements over the entire time.

The above control process functions in an analogous manner in the event that the barrier is formed by a covering which is arranged on the material with a liquid-absorbing structure and is configured, in the case of cooling of the device to a storage temperature which lies below the melting temperature of the indicator substance, to undergo a transition from a first state of the covering, in which it is impermeable with respect to the indicator substance, irreversibly into a second state of the covering, in which it is permeable for the indicator substance.

Figure 10:
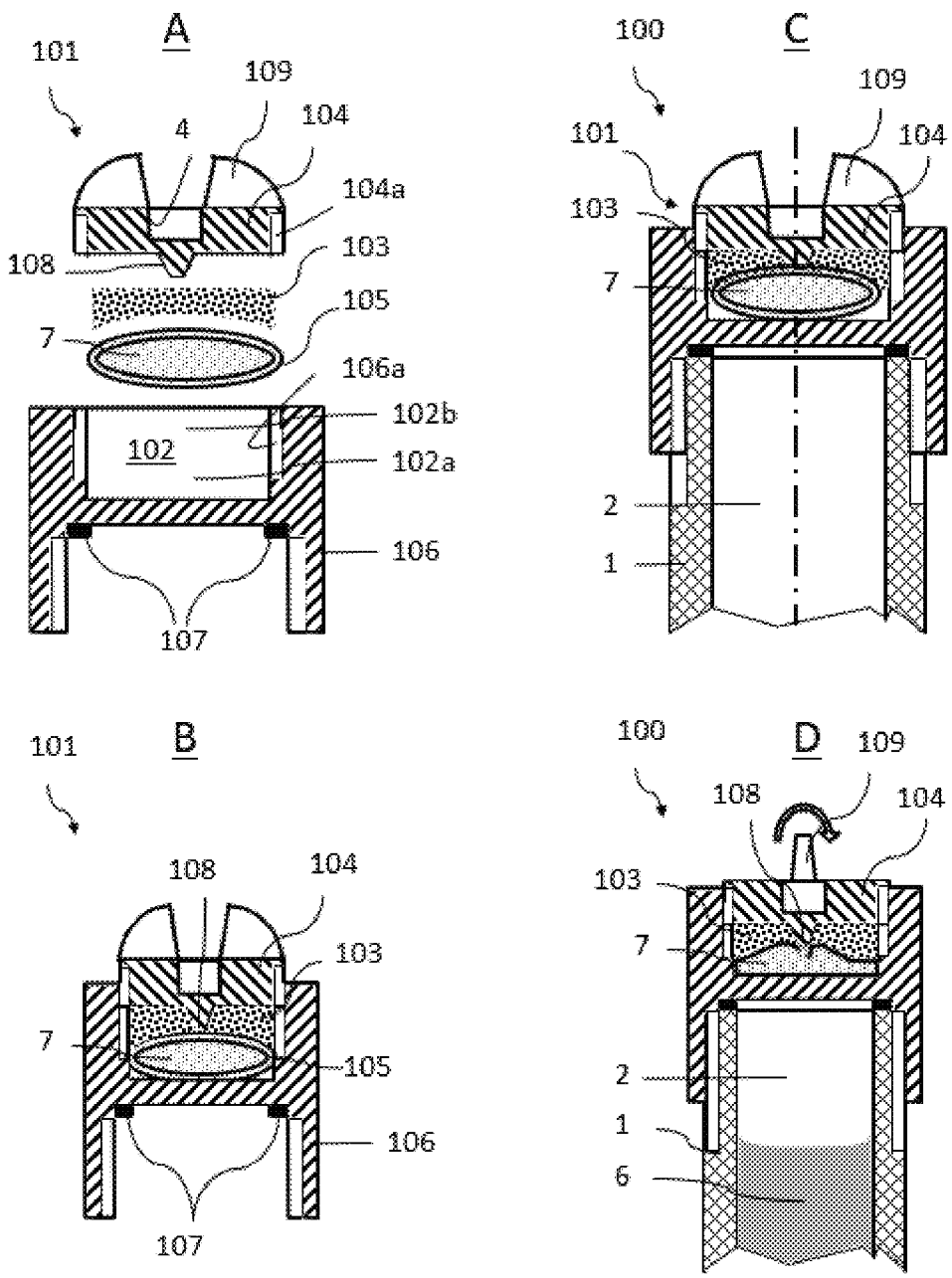
FIG. 10 shows an exemplary embodiment of a device for temperature monitoring.

FIG. 10 illustrates in several cross-sectional views a further exemplary embodiment 100 of a device for temperature monitoring. View A shows an exploded representation of a cover 101 of a cryogenic tube 1 in which an apparatus for temperature monitoring is integrated. Device 100 comprises cryogenic tube 1 with a receiving space 2 for receiving a biological sample 6 as well as cover 101 which has a chamber 102 which contains an indicator substance 7 which is separated by a barrier in the non-active state from an absorbent material 103. Cover 101 is also referred to below as a temperature-sensitive (T-sensitive) cover. View B shows cover 101 in the mounted state, view C illustrates a sale-ready cryogenic tube 1 with a receiving space 2 for receiving a biological sample 6 and with screwed-on T-sensitive cover 101. Views A to C show device 100 in the as yet inactivate state.

T-sensitive cover 101 comprises four parts: a screw insert 104, referred to below as screw-in part 104, an insert with a liquid-absorbing structure 103, referred to below as absorbent material 103, which must be able to suck up liquid indicator substance 7, a container 105 for indicator substance 7, here embodied by way of example as plastic cushion 105 which contains colored liquid as indicator substance 7 if this is not frozen, and a base body 106 for screwing onto a commercially available cryogenic tube 1, embodied here as plastic cap 106.

Plastic cushion 105 forms in the inactive state of device 100 an impervious sheath for indicator substance 7 located there and thus a barrier which, in the inactive state, prevents indicator substance 7 from being able to come into contact with absorbent material 103. The embodiment as a plastic cushion has the advantage that this can be produced at very low cost.

Screw-in part 104 is embodied to be transparent or semi-transparent at at least one point so that at least a part of absorbent material 103 can be seen from above through screw-in part 104. For this purpose, screw-in part 104 can, for example, be produced from a transparent or semi-transparent material. Moreover, for this purpose, base body 106 can be produced from a transparent or semi-transparent material. In this manner, it is possible to check by simple visual inspection from above whether the color state of absorbent material 103 has changed. This is e.g. the case if colored indicator substance 7 has penetrated into absorbent material 103 and thus is colored as a result, which will be described below.

The base body or plastic cap 106 has an H-shaped cross-section, as a result of which two cylindrical cavities are formed. Upper cavity 102 forms a chamber with a first sub-region 102a in which container 105 with indicator substance 7 is located, and with a second sub-region 102b in which absorbent material 13 is located.

The lower cavity serves to receive an upper end portion of cryogenic tube 1 in order to close it off tightly. Cryogenic tube 1 is sealed off with a sealing ring 107. An engagement 4, e.g. a hexagon hole, via which screw-in part 104 can be rotated into base body 106 is located in screw-in part 103. Screw-in part 104 may also have blades 109 via which screw-in part 104 can also be rotated. For screwing in, an external thread 104a is provided on screw-in part 104, which outer thread 104a engages into a corresponding internal thread 106 of base body 106 which is provided on a lateral wall of upper cavity 102.

As already mentioned, views A to C show device 100 in the as yet inactive state. This means that plastic cushion 105 filled with colored indicator substance is not destroyed and impervious so that indicator substance 7 in the liquid state cannot escape. Indicator substance 7 is initially located in liquid form in the interior of plastic cushion 105. Absorbent material 103 located thereabove is not in contact with indicator substance 7 as a result of intact plastic cushion 105. The indicator substance may contain, for example, one of the above-mentioned substances and be formed by a mixture of these substances. By way of example, indicator substance 7 may furthermore contain a dye as an indicator additive, e.g. the dye rhodamine B so that it is dyed red.

Screw-in part 104 is initially half screwed in (inactive state). In order to turn it further, e.g. a quarter or half turn, a plastic locking device in thread 103a, 106a must be broken through. It is thus ensured that the apparatus for temperature monitoring and/or the T-sensitive cover cannot be activated prior to use. Should this, however, occur prior to cryogenic storage of device 100 or sample 6, absorbent material 103 located in base body 106 becomes red and cannot consequently be used. The transport and interim storage of cover 101 in the inactive state can be carried out over any desired period of time, which is advantageous for trade and stock management.

View D of FIG. 10 shows the activation (switching into active mode) of the device after the storage temperature is reached, in the present case e.g. <−140° C.

Indicator substance 7 is selected so that it is no longer liquid at the storage temperature in container 105, but rather is already solidified. The activation (switching into active mode) of the device is performed by screwing in screw-in part 104 in the case of frozen indicator substance 7. Screw-in part 104 has, on its lower side facing absorbent material 103, a protruding projection 108, e.g. in the form or a tip or a thorn. By screwing in screw-in part 104, projection 108 is bored into plastic cushion 105 and destroys it. As a result, absorbent material 103 does not come into direct contact with red indicator substance 7. At the storage temperature, the indicator substance is so viscous or also solid that it is not absorbed into absorbent material 103. The still ongoing thermal shocks are also not sufficient for diffusion.

The device for temperature monitoring is thus activated (active). As soon as a transition temperature which indicates the melting point of the mixture of indicator substance 7 is exceeded during cryogenic storage, frozen indicator substance 7 becomes liquid. With rising temperature, the viscosity reduces until, at a threshold temperature, a threshold is exceeded from which absorbent material 103 pulls in the liquid via capillary forces and thus assumes its color. This process is irreversible, i.e. even after subsequent renewed freezing of indicator substance 7, the red coloring of absorbent material 103 is maintained. If it is subsequently ascertained in the case of a visual inspection that absorbent material 103 has a red coloring, it can be concluded that the melting temperature of the indicator substance and furthermore a slightly higher temperature than that of the melting temperature were likewise exceeded, in the case of which the viscosity of indicator substance 7 has become so low that it was pulled via capillary forces into absorbent material 103. The type and thickness of absorbent material 103 determines how quickly the recognizable coloring occurs. Absorbent material 103 may be, for example, filter paper, e.g. such as that of a conventional kitchen roll or a cigarette filter paper, a compact, cellulose discs, e.g. tissue cellulose disc, plaster and/or chalk dust.

That which applies to absorbent material 103 and indicator substance 7 in the interior of base body 106 also applies to the temperature in biosample 6. A red-colored absorbent material thus indicates that biosample 6 has also at least temporarily exceeded the above-mentioned temperatures. Since this process cannot be reversed even in the case of renewed deep-freezing, device 1 thus retains the information about unauthorized heating.

FIG. 11 illustrates in several cross-sectional views a further exemplary embodiment 110 of a device for temperature monitoring. Device 110 in turn comprises a cryogenic tube 1 with a receiving space 2 for receiving a biological sample 6 as well as a cover 111. The T-sensitive cover in turn comprises four parts: a screw insert 114, referred to below as screw-in part 114, an insert with a liquid-absorbing structure 113, referred to below as absorbent material 113, which must be able to suck up liquid indicator substance 7, and a container 105 for indicator substance 7 and a base body 116 for screwing onto a commercially available cryogenic tube 1, embodied here as plastic cap 116.

View A shows here cover 111 in the inactive state prior to mounting on cryogenic tube 1. View B shows an exploded representation of individual components of cover 111. View C shows device 110 in the active state.

In contrast to the embodiment variant represented in FIG. 10, the barrier is now not formed by a plastic cushion, but rather by a glass ball 115 which contains indicator substance 7. In order to fill glass ball 115 with indicator substance 7, it can have an opening 115a which is closed off by a closure 119 after filling with indicator substance 7, for example, by gluing opening 115a with a 2-component adhesive or by welding shut with cooling of indicator liquid 7. An absorbent material 113 is in turn placed on glass ball 115 closed in this manner which is not in contact with indicator substance 7 in this state (inactive state).

For activation of device 110 or switching it into active mode, it is initially cooled to storage temperature of cryogenic storage at which indicator substance 7 is frozen. Subsequently, in an analogous manner to that described above for the embodiment variant of FIG. 10, screw-in part 114 is rotated so far into plastic cap 116 until the barrier which separates indicator substance 7 from absorbent material 113 is destroyed. In the case of the exemplary embodiment shown in FIG. 11, this occurs in that, by means of a rotation of screw-in part 114, a projection 118 of the screw-in part protruding in the direction of glass ball 115 crushes glass ball 115. This activated or active state of device 110 is represented in illustration C. Indicator substance 7 is, however, selected so that at the storage temperature this is so viscous or also solid that it is not absorbed into absorbent material 103. The still ongoing thermal shocks are also not sufficient for diffusion. It is only when a transition temperature during cryogenic storage, which indicates e.g. the melting point of the mixture of indicator substance 7, is subsequently exceeded that frozen indicator substance 7 becomes liquid. With increasing temperature, the viscosity increasingly reduces until, at the threshold temperature, a threshold is exceeded from which absorbent material 113 at least partially draws in liquid indicator substance 7 via capillary forces and thus assumes its color.

One particular advantage of the embodiment of the barrier as glass ball 115 is that it makes a cracking noise during crushing so that, upon activation of device 110, an acoustic feedback signal is simultaneously generated that the device has now been switched into active mode.

FIG. 12 illustrates, in several views, a further exemplary embodiment 120 of a device for temperature monitoring. View A shows in this case a cross-sectional view of device 120 or of the complete cryogenic tube prior to activation (in the inactive state). View A1 shows a lower view of cryogenic tube 120. View B shows a cross-sectional view of device 120 in an exploded representation in order to illustrate the individual parts of device 120. View C shows a cross-section of device 120 in the activated state (active state).

Device 120 in turn comprises a cryogenic tube 1 with a receiving space 2, into which biological sample 6 is filled, as well as a screw-on cover 103 which is embodied here in a conventional manner and can have an engagement 4. The device in turn comprises an apparatus for temperature monitoring similar to that which was described in FIG. 10 or FIG. 11 for use in the screw cover. The particular feature of this exemplary embodiment lies in the fact that the apparatus for temperature monitoring is integrated into a lower part 121 of cryogenic tube 1, i.e. at the end region of cryogenic tube 1 opposite the cover. The advantage of this embodiment lies in the fact that, in contrast to the screw cover variant, there is no longer a simple possibility of replacing the apparatus for temperature monitoring since biological sample 6 is located in a frozen-sold state in this lower part and would also be removed.

The apparatus for temperature monitoring integrated into the lower part of the cryogenic tube comprises an absorbent material 123, an indicator substance 7, which is stored initially in the liquid state in a closed off ellipsoid container 105, composed e.g. of plastic or glass, and a plastic base part 125 at the base of cryogenic tube 1 which has an opening 27 in which a round part 124, which can be pushed upwards once, is located, on the underside of which round part a conventional 2D barcode 126 is imprinted. On the side facing away from the barcode, part 124 has a cylindrical, slightly conical thorn 128. Part 124 is also referred to below as tappet 124. Tappet 124 and preferably also plastic base part 125 are produced from a transparent or semi-transparent material. Indicator substance 7 can again contain a dye as the indicator additive, e.g. the dye rhodamine B so that it is colored red.

In the manufacturing process, the parts are mounted as follows: container 105 with indicator substance 7 is inserted into a depression 122 at the base of tube 1. The depression is curved at its side at the top in FIG. 12 with a form corresponding to indicator substance container 105. Absorbent material 123 is placed above this. Depression 122 thus forms a chamber for receiving indicator substance container 105 and absorbent material 123.

Plastic base part 125 is now put in place and connected fixedly and preferably undetachably to cryogenic tube 1, e.g. by welding on or gluing on.

Tappet 124 with barcode 126 is pushed in so far that it penetrates precisely with thorn 128 into absorbent material 123, but not into indicator substance container 105. For example, this can be achieved in that cryogenic tube 1 is pushed perpendicularly onto tappet 124 until it terminates flush with the base surface of plastic base part 125, as is shown in view A. The user is provided, as is also currently the case, with two parts mounted: cover 3 and joined lower part 1, 121 comprising the cryogenic tube, tappet 124, indicator substance container 105, absorbent material 123, plastic base part 125 and barcode 126. In this state, the apparatus for temperature monitoring at the base is not activated (inactive).

In the event of use, the user fills biosample 6 into lower part 1, 121, cools the tube to the storage temperature and then presses tappet 124 with force on the base upwards up to stop 129 (illustrated by the arrow in view C).

As a result, receptacle 105 of frozen indicator liquid 7 is destroyed and absorbent material 123 is pushed onto this. Slightly conical tappet 124 seals off opening 127 through which it moves. A coating can optionally also be applied on tappet 124, which coating leads to gas-impervious closing off. Device 120 is now activated.

Indicator substance 7 is in turn selected so that it, at the storage temperature in container 105, is no longer liquid, but rather is already solidified or is at least so viscous or also solid that it is not drawn into absorbent material 123. The still ongoing thermal shocks are also not sufficient for diffusion.

As soon as a transition temperature which indicates the melting point of indicator substance 7 is exceeded during cryogenic storage, frozen indicator substance 7 becomes liquid. With rising temperature, the viscosity reduces until a threshold temperature is exceeded from which absorbent material 123 draws in indicator liquid 7 via capillary forces and thus assumes its color. This process is irreversible, i.e. even after subsequent renewed freezing of indicator substance 7, the red coloring of absorbent material 123 is maintained.

If the first or second threshold value temperature to be monitored is not exceeded, the base of the cryogenic tube remains unchanged in color (e.g. white, shown in view C1). This is illustrated in view C1 which shows a lower view of cryogenic tube 120 in a state in which the indicator substance was not drawn into the absorbent material. If, however, the second threshold value temperature is not exceeded during storage of activated device 120, absorbent material 123 fills up, and base 121 of the cryogenic tube, in particular tappet 124, appears colored, e.g. colored red. This is illustrated in view C2 which shows a lower view of cryogenic tube 120 in a state, in the case of which indicator substance 7 was drawn into the absorbent material. This embodiment is also advantageous because such barcode tubes are already widely available and therefore the coloring at the base can be easily read if barcode identification is carried out.

Although the invention has been described with reference to specific exemplary embodiments, it is apparent for a person skilled in the art that various changes can be made and equivalents can be used as a replacement without departing from the scope of the invention. The invention should consequently not be restricted to the disclosed exemplary embodiments, but rather should enclose all the exemplary embodiments which fall into the scope of the enclosed claims. In particular, the invention also claims protection for the subject matter and the features of the subordinate claims independently of the claims referred to.

The invention claimed is:
1. A device for temperature monitoring of a cryopreserved biological sample, comprising
   a) a sample container with a receiving space for receiving a biological sample; and
   b) at least one chamber, an inner space of which is not fluidically connected to the receiving space and is only partially filled with an indicator substance, a melting temperature of which lies in a range from −20° C. to −140° C.,
   wherein when the indicator substance is located in a first sub-region of the chamber in a liquid state, a barrier of the at least one chamber is configured to delay passage of the indicator substance from the first sub-region into a second sub-region of the at least one chamber indicating temperature change,
   wherein the device is configured in accordance with:
   (i) a first variant wherein the indicator substance is stored in a receptacle which tightly encloses the indicator substance in the liquid state; and the device has an activation part which is guided movably in relation to the receptacle and which can be moved from a starting position into an the activation position, wherein the movement into the activation position brings about that the activation part, as a result of mechanical pressure, destroys the receptacle at at least one point such that the receptacle becomes permeable for the indicator substance in the liquid state; or
   (ii) a second variant wherein the barrier is a separating element which is permeable in relation to the indicator substance in the liquid state and which is arranged between the first sub-region and second sub-region; wherein the separating element is configured, in a case of cooling of the device to a storage temperature which lies below the melting temperature of the indicator substance, to tear at at least one point as a result of thermal contraction to form an opening so that the indicator substance can pass in the liquid state via the opening from the first sub-region into the second sub-region.

2. The device according to claim 1, wherein the device is configured in accordance with the first variant, and the barrier is a material, which is arranged in the second sub-region and adjoins the first sub-region, with a liquid-absorbing structure.

3. The device according to claim 2, wherein a structure and/or a composition of the material with a liquid-absorbing structure is formed so that a diffusion speed of the indicator substance in the material reduces non-linearly with increasing distance from the first sub-region.

4. The device according to claim 1, wherein the device is configured in accordance with the first variant, and the receptacle is a plastic cushion or as a glass ball.

5. The device according to claim 1, wherein the sample container has a cover for closing off the receiving space, wherein the at least one chamber is integrated into the cover.

6. The device according to claim 5, wherein the cover has a base body with an H-shaped cross-section, which can be pushed and/or screwed onto the sample container, wherein the base body has, for formation of the at least one chamber, a recess in which the receptacle with the indicator substance and the material with a liquid-absorbing structure are arranged, wherein the activation part is a screw-on part, on the base body is guided movably in a direction of the receptacle.

7. The device according to claim 5, wherein the cover comprises a shaft which is in engagement with an upper end region of the receiving space and that the at least one chamber is integrated into the shaft.

8. The device according to claim 1, wherein the at least one chamber of the device is integrated into a base region of the sample container.

9. The device according to claim 8, wherein the device is configured in accordance with the first variant, and the base region of the sample container has, for formation of the at least one chamber, a recess in which the receptacle with the indicator substance and the material with a liquid-absorbing structure are arranged, wherein the recess is closed off by a base part in which the activation part is guided movably.

10. The device according to claim 9, wherein
    a) the activation position is fixed by a stop formed by the base part, up to which stop the activation part can be pushed into the base part; and/or
    b) the base part is connected fixedly to the base region of the sample container.

11. The device according to claim 1, wherein a wall of the second sub-region of the chamber and/or a wall of the first sub-region of the chamber
    a) comprises a scale which displays a fill level of the indicator substance in the respective sub-region or a duration of the exceeding of the melting temperature; and/or
    b) is transparent or semi-transparent at at least one point.

12. The device according to claim 1, wherein the device is configured in accordance with the second variant, and the separating element which is permeable in relation to the indicator substance in the liquid state is a porous separating wall, membrane, film, skin or capillary system.

13. The device according to claim 12, wherein the separating element has at least one predetermined breaking point at which the separating element tears during cooling of the device to the storage temperature.

14. The device according to claim 1, wherein the device is configured in accordance with the second variant, and in the second sub-region
    a) a gas is present, or
    b) a substance which has a lower melting point than the indicator substance is present.

15. The device according to claim 1, wherein an outer wall of the chamber has a closable opening to the first sub-region for filling the first sub-region with an indicator substance.

16. The device according to claim 1, wherein
    a) the at least one chamber is formed by a container; and
    b) there is fastened to an outer wall of the sample container a receiver into which the container can be inserted and/or is inserted for retention on the sample container.

17. The device according to claim 1, wherein
    a) the sample container is a cryogenic tube; and
    b) the at least one chamber is formed by a double-walled push-on part which can be pushed onto an outer shell surface of the cryogenic tube and at least partially engages around the outer shell surface of the cryogenic tube in the pushed-on state.

18. The device according to claim 17, wherein the sample container is glued, melted or fixed solidly in another manner to the push-on part.

19. The device according to claim 1, wherein the sample container is a bag for storing blood samples or stem cells which is retained in a cassette, wherein the at least one chamber is formed by a container, which
  a) is fastened to an outer side of the bag,
  b) is present floating freely in an interior of the bag or
  c) is fastened to the cassette.

20. A method for temperature monitoring of cryopreserved samples, comprising the steps:
  a) providing a device for temperature monitoring according to claim 1, which contains at least one indicator substance in a frozen state in the first sub-region of the chamber, wherein the receiving space contains a cryopreserved sample;
  b) cooled storing of the device for cryopreservation; and
  c) checking whether the indicator substance is located in the second sub-region of the chamber at a later point in time.

21. The method according to claim 20, further comprising determining a parameter which indicates a measure of a quantity of indicator substance which has moved into the second sub-region of the chamber and/or a measure of the quantity of indicator substance located in the first sub-region of the chamber.

22. The method according to claim 20, wherein the indicator substance has a melting temperature or a threshold temperature at which a viscosity of the melted indicator substance undershoots a specific target value, which corresponds to a predetermined threshold temperature, and the method further comprises monitoring whether the predetermined threshold temperature is exceeded.

23. The method according to claim 20, wherein
  a) the device provided for temperature monitoring has a covering, a cover, a base region or a separating element;
  b) at least one of the following test steps is carried out in order to check a functionality of the device for temperature monitoring:
    b1) testing whether the second sub-region of the at least one chamber is free from indicator substance after filling of the first sub-region with indicator substance and prior to freezing of the indicator substance;
    b2) testing whether the second sub-region of the at least one chamber is free from indicator substance after freezing of the indicator substance located in the first sub-region of the at least one chamber and prior to cooled storage of the device for cryopreservation; or
    b3) if a cryopreserved sample is removed for use and if no indicator substance is then located in the second sub-region of the chamber, testing whether the covering has correctly transferred into the permeable second state or whether the separating element of the at least one chamber is correctly torn.

24. The device according to claim 1, wherein the indicator substance comprises at least one alcohol selected from the group consisting of octan-1-ol, nonan-1-ol, propane-1,2-diol, propane-1,3-diol, butane-1,2-diol, butane-1,3-diol, butan-2-ol, pentane-1,5-diol, pentan-1-ol, cyclopentanol, and benzyl alcohol as well as optionally at least one dye.

25. The device according to claim 24, wherein the dye is selected from the group consisting of triphenylmethane dyes, rhodamine dyes, azo dyes, phenazine dyes and phenothiazine dyes.

26. The device or method according to claim 24, wherein the indicator substance comprises at least two alcohol components which are selected from the group consisting of octan-1-ol, nonan-1-ol, propane-1,2-diol, propane-1,3-diol, butane-1,2-diol, butane-1,3-diol, butan-2-ol, pentane-1,5-diol, pentan-1-ol, cyclopentanol, and benzyl alcohol and/or the indicator substance comprises at least one dye selected from the group consisting of oil red, methyl red, brilliant green, rhodamine B, neutral red, and methylene blue.

27. The device according to claim 5, wherein the base part has a machine-readable code and/or an optoelectronically readable code, which is a barcode or a 2D code.

* * * * *